(12) United States Patent
Wainrib et al.

(10) Patent No.: US 11,544,851 B2
(45) Date of Patent: Jan. 3, 2023

(54) SYSTEMS AND METHODS FOR MESOTHELIOMA FEATURE DETECTION AND ENHANCED PROGNOSIS OR RESPONSE TO TREATMENT

(71) Applicants: Owkin Inc., New York, NY (US); Owkin France SAS, Paris (FR); Centre Léon Bérard, Lyons (FR)

(72) Inventors: Gilles Wainrib, Pantin (FR); Thomas Clozel, New York, NY (US); Pierre Courtiol, Paris (FR); Charles Maussion, Paris (FR); Jean-Yves Blay, Lyons (FR); Françoise Galateau Sallé, Caen (FR)

(73) Assignees: OWKIN, INC., New York, NY (US); OWKIN FRANCE SAS, Paris (FR)

( * ) Notice: Subject to any disclaimer, the term of this patent is extended or adjusted under 35 U.S.C. 154(b) by 0 days.

(21) Appl. No.: 17/185,924

(22) Filed: Feb. 25, 2021

(65) Prior Publication Data

US 2021/0256699 A1    Aug. 19, 2021

Related U.S. Application Data

(63) Continuation of application No. PCT/IB2020/056030, filed on Jun. 25, 2020.

(30) Foreign Application Priority Data

Jun. 25, 2019  (EP) .................................... 19305839

(51) Int. Cl.
*G06T 7/00* (2017.01)
*G06T 7/194* (2017.01)
(Continued)

(52) U.S. Cl.
CPC ............. *G06T 7/0014* (2013.01); *G06N 3/08* (2013.01); *G06T 7/11* (2017.01); *G06T 7/194* (2017.01);
(Continued)

(58) Field of Classification Search
None
See application file for complete search history.

(56) References Cited

U.S. PATENT DOCUMENTS 9,739,783 B1 * 8/2017 Kumar ............. G01N 33/57415
10,496,884 B1 * 12/2019 Nguyen ............... G06N 3/0454
(Continued)

FOREIGN PATENT DOCUMENTS

WO    WO-2018200715 A1 * 11/2018    ........... G06K 9/6273

OTHER PUBLICATIONS

Al-Bahrani R, Agrawal A, Choudhary A. "Survivability prediction of colon cancer patients using neural networks." doi:10.1177/1460458217720395; Sep. 2017 (Year: 2017).*
(Continued)

*Primary Examiner* — Jiangeng Sun
(74) *Attorney, Agent, or Firm* — Womble Bond Dickinson (US) LLP

(57) ABSTRACT

A method and apparatus of a device that classifies a mesothelioma image is described. In an exemplary embodiment, the device segments the mesothelioma image into a region of interest that includes information useful for classification, and a background region, by applying a first convolutional neural network. In addition, the device tiles the region of
(Continued)

interest into a set of tiles. For each tile, the device extracts a feature vector of that tile by applying a second convolutional neural network, where the features of the feature vectors represent local descriptors of the tile. Furthermore, the device processes the extracted feature vectors of the set of tiles to classify the image.

**30 Claims, 28 Drawing Sheets
(14 of 28 Drawing Sheet(s) Filed in Color)**

(51) Int. Cl.
  *G06T 7/11* (2017.01)
  *G16H 30/20* (2018.01)
  *G06N 3/08* (2006.01)

(52) U.S. Cl.
  CPC ... *G16H 30/20* (2018.01); *G06T 2207/10056* (2013.01); *G06T 2207/20021* (2013.01); *G06T 2207/20081* (2013.01); *G06T 2207/20084* (2013.01); *G06T 2207/30024* (2013.01)

(56) References Cited

U.S. PATENT DOCUMENTS

| | | | | |
|---|---|---|---|---|
| 2002/0186875 | A1* | 12/2002 | Burmer | G06K 9/66 382/133 |
| 2015/0065803 | A1* | 3/2015 | Douglas | A61B 1/00045 600/200 |
| 2018/0315193 | A1* | 11/2018 | Paschalakis | G06N 3/08 |
| 2019/0147221 | A1* | 5/2019 | Grabner | G06T 7/75 382/103 |
| 2019/0304092 | A1* | 10/2019 | Akselrod-Ballin | G06T 7/13 |
| 2020/0349707 | A1* | 11/2020 | Hosseini | G16H 50/20 |

OTHER PUBLICATIONS

"Written Opinion and International Search Report," for PCT/IB2020/056030 dated Nov. 2, 2020 (18 pages).

"International Preliminary Report on Patentability," for PCT/IB2020/056030 dated Dec. 28, 2021 (14 pages).

Pierre Courtiol et al., "Classification and Disease Localization in Histopathology Using Only Global Labels: A Weakly-Supervised Approach," Arxiv.org, Cornell Univesity Library, 201 Olin Library Cornell University, Ithaca, NY 14853 (Feb. 1, 2018).

Peter Bandi et al., "Comparison of different methods for tissue segmentation in hitopathological whole-slide images," 2017 IEEE 14th International Symposium on Biomedical Imaging (ISBI), pp. 591-595 (Apr. 1, 2017).

Anindya Gupta et al., "Deep Learning in Image Cytometry: A Review," NIH Public Access Author Manuscript, vol. 95, No. 4, pp. 366-380 (Dec. 19, 2018).

Dmitrii Bychkov et al., Deep learning based tissue analysis predicts outcome in colorectal cancer, Scientific Reports, vol. 8, No. 1 (Feb. 21, 2018).

Lee Add Cooper et al., "PanCancer insights from The Cancer Genome Atlas: the pathologist's perspective: Insights from TCGA: PanCancer and digital pathology anlyses," The Journal of Pathology, vol. 244, No. 5, pp. 512-524 (Feb. 22, 2018).

Francesco Ponzio et al., "Dealing with Lack of Training Data for Convolutional Neural Networks: The Case of Digital Pathology," Electronics, vol. 8, No. 3, p. 256 (Feb. 26, 2019).

Courtiol Pierre et al., "Deep learning-based classification of mesothelioma improves prediction of patient outcome," Nature Medicine, Nature Pub. Co., New York, vol. 25, No. 10 (Abstract) (Oct. 1, 2019).

Le Hou et al., "Patch-Based Convolutional Neural Network for Whole Slide tissue Image Classification," 2016 IEEE Conference on Computer Vision and Pattern Recognition (CVPR), pp. 2424-2433 (Jun. 1, 2016).

European Search Report for counterpart Application No. EP 19305839 dated Jul. 17, 2020 (8 pages).

* cited by examiner

SYSTEMS AND METHODS FOR MESOTHELIOMA FEATURE DETECTION AND ENHANCED PROGNOSIS OR RESPONSE TO TREATMENT

RELATED APPLICATIONS

This application is a continuation of International Application No. PCT/IB2020/056030, filed on Jun. 25, 2020, which claims the benefit of priority to European Patent Application Number EP19305839.3, filed on Jun. 25, 2019. The entire contents of the foregoing applications are hereby incorporated herein by reference.

BACKGROUND

Malignant mesothelioma (MM) is a rare but highly lethal cancer. It is derived from the lining of the serous cavities, and is associated with asbestos exposure in 80% of cases. (Noonan, C. W. Environmental asbestos exposure and mesothelioma. *Ann. Transl. Med.* 5, 234, 2017; Lacourt, A. et al. Dose-time-response association between occupational asbestos exposure and pleural mesothelioma. *Occup. Environ. Med.* 74, 691-697, 2017). It can be latent for several decades and, although strict regulations regarding asbestos use have been put in place in Europe and the US, its incidence rate is still expected to increase over the next several years. (Robinson, B. W. S. & Lake, R. A. Advances in Malignant Mesothelioma. *N. Engl. J. Med.* 353, 1591-1603, 2005).

MM is an aggressive cancer primarily diagnosed on the basis of histological criteria. Current diagnosis is established by a pathologist through tissue biopsy, and patients are segregated according to the World Health Organization's 2015 classification into three subtypes: epithelioid MM (EMM), sarcomatoid MM (SMM), or biphasic MM (BMM), which contains a mix of both sarcomatoid and epithelioid components. This histological classification serves as the current best practice to predict patient outcome, and can be used to select therapeutic options. (Opitz, I. et al. A new prognostic score supporting treatment allocation for multimodality therapy for malignant pleural mesothelioma: A review of 12 years' experience. *J. Thorac. Oncol.* 10, 1634-1641, 2015; Kindler, H. L. et al. Treatment of malignant pleural mesothelioma: American society of clinical oncology clinical practice guideline. *J. Clin. Oncol.* 36, 1343-1373, 2018).

Median overall survival across all mesothelioma patients ranges from 8 to 36 months. EMM patients have the most favorable prognosis, with a median survival of 16 months, followed by BMM and then SMM patients, who have the worst prognosis, with a median survival of five months. (Yap, T. A., Aerts, J. G., Popat, S. & Fennell, D. A. Novel insights into mesothelioma biology and implications for therapy. *Nat. Rev. Cancer* 17, 475-488, 2017). However, current histological criteria for diagnosing and subtyping MM are associated with significant inter-observer variability between pathologists, which in many cases leads to reduced predictive performance and sub-optimal patient care. (Galateau-Salle, F. et al. New Insights on Diagnostic Reproducibility of Biphasic Mesotheliomas: A Multi-Institutional Evaluation by the International Mesothelioma Panel From the MESOPATH Reference Center. *J. Thorac. Oncol.* 13, 1189-1203, 2018). Reproducibility issues, as well as the provisional introduction of new subtypes, call for the establishment of new methods to identify predictive biomarkers consistently associated with survival. (Brcic, L., Vlacic, G., Quehenberger, F. & Kern, I. Reproducibility of malignant pleural mesothelioma histopathologic subtyping. *Arch. Pathol. Lab. Med.* 142, 747-752, 2018; Hmeljak, J. et al. Integrative Molecular Characterization of Malignant Pleural Mesothelioma. *Cancer Discov.* CD-18-0804 (2018). doi: 10.1158/2159-8290.CD-18-0804; Shrestha, R. et al. BAP1 Loss Predicts Therapeutic Vulnerability in Malignant Peritoneal Mesothelioma. *bioRxiv,* 2018 doi:http://dx.doi.org/10.1101/243477).

SUMMARY OF THE INVENTION

A new approach based on deep convolutional neural networks (CNNs) described herein can accurately predict the overall survival (OS) of mesothelioma patients from tumor histology. This approach is more accurate than current pathology practices and classical predictive models, and generalizes well to an independent cohort. The model described herein can be used to analyze very large whole slide images (WSIs) without any pathologist-provided locally annotated regions. Unlike traditional black-box deep learning methods, this model can identify regions of the image that contribute to the prediction.

Accordingly, in one aspect, the invention provides a method for determining the prognosis of a subject known or suspected to have mesothelioma. This method can comprise accessing a biopsy image obtained from the subject; extracting a plurality of feature vectors of the biopsy image by applying a first convolutional neural network, where each of the features of the plurality of feature vectors represents local descriptors of the biopsy image; classifying the biopsy image using at least the plurality of feature vectors and a classification model, where the classification model is trained using a training set of known mesothelioma images and known mesothelioma prognosis indications; and determining the prognosis of the subject based on at least the classification of the biopsy image.

In one embodiment, the biopsy image is one of a digitized whole slide image (WSI) and a digitized image of a pathology section obtained from a biopsy stained with hematoxylin and eosin (H&E).

In another embodiment, the method can further comprise segmenting the biopsy image into a region of interest that includes information useful for classification, and a background region, by applying a second convolutional neural network. The second convolutional neural network can be, for example, a U-NET neural network. In one embodiment, the region of interest is a tumor region indicative of mesothelioma, and/or a stromal region indicative of mesothelioma.

In one embodiment, the method can further comprise tiling a region on interest of the biopsy image into a set of tiles, where each of the plurality of feature vectors corresponds to a tile from the set of tiles.

In one embodiment, the tiling comprises applying a fixed tiling grid to at least the region of interest, where each of the set of tiles has a predetermined size. In another embodiment, the tile scoring comprises computing a score for each tile in the set of tiles using at least a convolutional 1D layer and the corresponding feature vector for that tile. The classification can comprise, for example, applying the classification model to a subset of tile scores to classify the biopsy image. In one embodiment, the classification model is a multi-layer perceptron, with two connected layers.

In another embodiment, the tiling can further comprise determining the subset of tile scores by (i) picking a highest set of tile scores, and (ii) picking a lowest set of tile scores.

The first convolutional neural network can be, in some embodiments, a ResNet50 neural network.

In one embodiment, the extraction can further comprise applying an autoencoder on the extracted plurality of feature vectors to reduce a dimensionality of the features of the plurality of feature vectors.

In some embodiments, the training set of known mesothelioma images lacks local annotations of histopathological features. In some embodiments, the biopsy image lacks local annotations of histopathological features.

In some embodiments, the known mesothelioma prognosis indications represent the duration of survival associated with the known mesothelioma images.

In one embodiment, the prognosis of the subject is a risk score.

In one embodiment, the risk score represents an estimated survival duration.

In another aspect, the invention provides a method for determining the prognosis of a subject known or suspected to have mesothelioma. The method can comprise accessing a biopsy image obtained from the subject; identifying a tumor region of the biopsy image indicative of mesothelioma; and defining a set of discriminative features of a stromal region adjacent to the tumor region of the biopsy image, wherein the set of discriminative features includes one or more of stromal cell architecture, inflammatory response, and stromal vascularization; where a heavily pleomorphic stromal cell architecture, a low inflammatory response, and/or a poorly-vascularized stromal region is indicative that the subject has a prognosis of low survival; and where the absence of a heavily pleomorphic stromal cell architecture, a high inflammatory response, and/or a well-vascularized stromal region is indicative that the subject has a prognosis of high survival.

In one embodiment of the invention, the prognosis of low survival indicates that the subject is likely to survive less than 20 months from the time of biopsy. In another embodiment, the prognosis of high survival indicates that the subject is likely to survive greater than 20 months from the time of biopsy.

In one embodiment, the set of discriminative features is determined on subsets of the biopsy images using a computer program comprising code instructions for extracting a plurality of feature vectors of the biopsy image.

In another embodiment, the prognosis of the subject is made using a computer program comprising code instructions for executing a classification algorithm. The classification algorithm can determine a classification based on at least the plurality of feature vectors, and the classification is trained using at least a set of training images, where the set of training images comprises a set of biopsy images obtained from a plurality of mesothelioma subjects of known survival duration.

In another embodiment, the classification algorithm computes a set of scores for the subject, where the set of scores is indicative of the duration of survival of the subject.

In one embodiment, the foregoing methods can further comprise determining the presence of sarcomatoid and/or epithelioid components in the biopsy image. In another embodiment, the foregoing methods can further comprise determining the grade of the tumor present in the tumor region of the biopsy image.

In one embodiment, the biopsy image is a digitized while slide image (WSI). For example, the biopsy image can be a digitized image of a pathology section obtained from a biopsy stained with hematoxylin and eosin (H&E). In some embodiments, the biopsy is a needle biopsy, an endoscopic biopsy, or a surgical biopsy. In exemplary embodiments, the biopsy is a thoracentesis biopsy, a thoracoscopy biopsy, or a thoracotomy biopsy. In other exemplary embodiments, the biopsy is a paracentesis biopsy, a lararoscopy biopsy, or a laparotomy biopsy.

In another aspect, the invention provides a method for generating a classification model for mesothelioma prognosis prediction. The method can comprise receiving a training set of biopsy images, where each of the training set of biopsy images has an associated known classification. For each of the biopsy images in the training set of biopsy images, a plurality of feature vectors are extracted of the biopsy image by applying a first convolutional neural network, where each of the features of the plurality of feature vectors represents local descriptors of that biopsy image. A training score set for that biopsy image can be generated using at least the plurality feature vectors. The classification model can be trained using at least the training score sets of the plurality of biopsy images, and the associated known classifications.

In one embodiment, the first convolutional neural network is a ResNet50 neural network.

In one embodiment, the classification model is validated using at least a validation set of biopsy images. In some embodiments, the validation can comprise (a) receiving the validation set of biopsy images, wherein each of the validation set of biopsy images has an associated known classification; (b) for each of the biopsy images in the validation set of biopsy images, (i) extracting a plurality of feature vectors of that biopsy image by applying a first convolutional neural network, wherein each of the features of the plurality of feature vectors represents local descriptors of that biopsy image; (ii) generating a validation score set for that biopsy image using at least the plurality feature vectors, and (iii) generating a classification for that biopsy image using at least the validation score set and the classification model; and (c) comparing the plurality of generated classifications with the associated known classifications.

In one embodiment, the comparison of the plurality of generated classifications is performed using an area under the receiver operating characteristic curve (ROC-AUC) comparison, an area under the precision recall curve (PR-AUC) comparison, or a concordance index (c-index) comparison.

In another embodiment, each of the training set of biopsy images and the validation set of biopsy images is selected from the MESOPATH/MESOBANK dataset.

In another embodiment, the classification model is a multi-layer perceptron with two connected layers.

In one embodiment, a biopsy image of the training set or validation set is one of a digitized whole slide image (WSI), and a digitized image of a pathology section from a biopsy stained with hematoxylin and eosin (H&E).

In some embodiments, each of the associated known classifications is a known mesothelioma survival value.

In another embodiment, the step of extracting of the plurality of feature vectors comprises tiling a region of interest of that biopsy image into a set of tiles, where each of the plurality of feature vectors corresponds to a tile from the set of tiles.

In another embodiment, the step of tiling comprises applying a fixed tiling grid to at least the region of interest, wherein each of the set of tiles has a predetermined size.

In another embodiment, the step of generating a training score set for that biopsy image comprises computing a score for each tile in the set of tiles using at least a convolutional 1D layer and the corresponding feature vector for that tile.

In another embodiment, for each of the biopsy images in the training set of biopsy images, the method can further comprise segmenting the biopsy image into a region of interest that includes information useful for classification and a background region, by applying a second convolutional neural network. The second convolutional neural network can be, for example, a U-Net neural network. In some embodiments, the region of interest is a tumor region and/or a stromal region indicative of mesothelioma.

In another aspect, the invention provides a method of determining a mesothelioma histological predictive feature, comprising (a) receiving a training set of biopsy images, wherein each of the training set of biopsy images has an associated known mesothelioma survival value; (b) for each of the biopsy images in the training set of images, (i) tiling a region of interest of that biopsy image into a set of tiles, (ii) extracting a plurality of feature vectors of the biopsy image corresponding to the set of tiles by applying a first convolutional neural network, wherein each of the features of the plurality of feature vectors represents local descriptors of that biopsy image, and (iii) generating a score for each tile in the set of tiles for that biopsy image using at least the plurality feature vectors; (c) selecting a predictive set of tiles from the training set of images based on at least the scores for each tile in the predictive set of tiles; and (d) correlating the associated mesothelioma survival value of the predictive set of tiles with histological features of the predictive set of tiles to determine a mesothelioma histological predictive feature.

In one embodiment, the predictive set of tiles includes predictive and non-predictive tiles that are similar based on a vector of coefficient.

In another embodiment, the step of correlating includes comparing histological features of the predictive and non-predictive tiles.

In one embodiment, the predictive set of tiles includes at least one of a tile associated with a low survival value. For example, a mesothelioma histological predictive feature of a tile with a low survival value can be a higher grade tumor, more pleomorphic, atypical, and shows a lower inflammatory response, relative to a non-predictive tile. In another example, having a sarcomatoid pattern can be a mesothelioma histological predictive feature of a tile with a low survival value.

In another embodiment, the predictive set of tiles includes at least one of a tile associated with a high survival value. For example, a mesothelioma histological predictive feature of a tile with a high survival value is a lower grade tumor, less pleomorphic, atypical, and shows a greater inflammatory response, relative to a non-predictive tile.

BRIEF DESCRIPTION OF THE DRAWINGS

The present invention is illustrated by way of example and not limitation in the figures of the accompanying drawings in which like references indicate similar elements. The patent or application file contains at least one drawing executed in color. Copies of this patent or patent application publication with color drawing(s) will be provided by the Office upon request and payment of the necessary fee.

FIG. 13a shows a distribution of the c-index for the different predictive models on the Training, Test, and TCGA datasets. FIG. 13b shows a histological repartition of the 60 patients from the test dataset with the worst prognosis as predicted by MesoNet, and comparison of the outcome for the 60 sarcomatoid patients. FIG. 13c demonstrates a grade distribution of the 80 patients from the test dataset with the best prognosis as predicted by MesoNet and comparison with the outcome for the 80 grade 1 epithelioid patients. FIG. 13d displays a survival analysis of the whole test dataset (vs the EMM test dataset) on the left (vs the right), split evenly into three subgroups of high, intermediate, and low survival based on the prediction of MesoNet. FIG. 13e displays a survival analysis of grade 1, 2, and 3 EMM patients, split evenly into two subgroups based on the prediction of MesoNet.

FIG. 14a is a distribution of tile scores obtained from a WSI using MesoNet for a patient with a good (on top) vs bad (on the bottom) prognosis and aggregated in a single distribution for all patients in the MESOPATH/MESOBANK dataset in the middle. FIG. 14b is an extraction of the extremal tiles associated with overall high and low survival for all mesothelioma patients to be reviewed by a pathologist.

FIG. 15a shows a schematic representation of the reviewing process. FIG. 15b is a repartition of features of interest in low and high survival tiles. FIG. 15c displays tiles of low survival with a transitional pattern. FIG. 15d shows tiles of unknown significance "TUS".

FIG. 18a show extremal tiles associated with low survival were mostly composed of epithelioid and sarcomatoid patterns, but a few were composed of transitional patterns and patterns of unknown significance. FIG. 18b display extremal tiles located primarily in stromal regions. FIG. 18c shows various visualized scenarios predicted by MesoNet. Although the first epithelioid patient had a very poor prognosis, the predictive tiles were composed of epithelioid components only.

DETAILED DESCRIPTION

Figure 1:
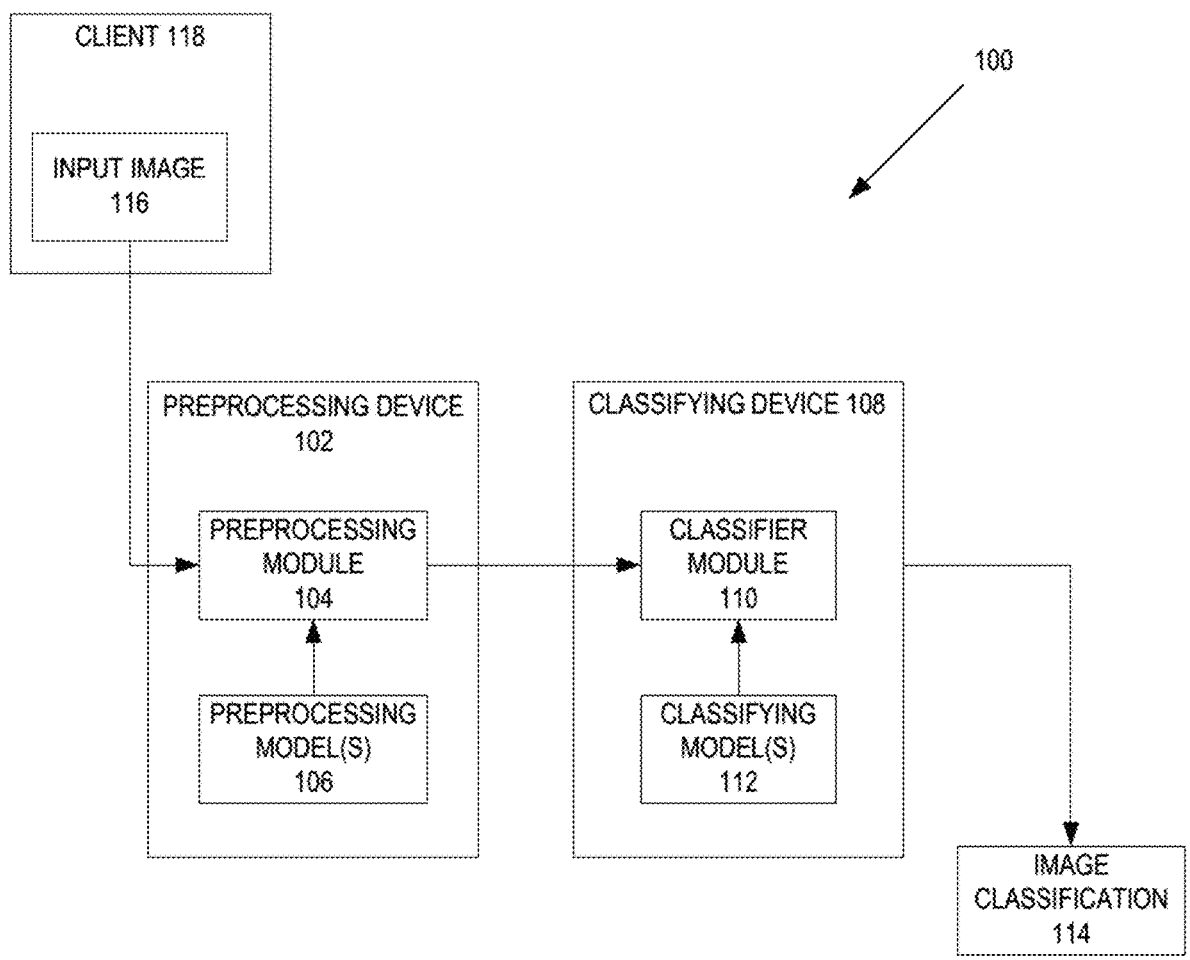
FIG. 1 is a block diagram of one embodiment of a system for classifying a mesothelioma histopathology image by preprocessing the image using a classification model.

A method and apparatus of a device that classifies a mesothelioma image derived from a mesothelioma patient is described herein. In the following description, numerous specific details are set forth to provide thorough explanation of embodiments of the present invention. It will be apparent, however, to one skilled in the art, that embodiments of the present invention may be practiced without these specific details. In other instances, well-known components, structures, and techniques have not been shown in detail in order not to obscure the understanding of this description.

In order that the present invention may be more readily understood, certain term are first defined.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

The use of the terms "a" and "an" and "the" and similar referents in the context of describing the invention (especially in the context of the following claims) are to be construed to cover both the singular and the plural (i.e., one or more), unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited.

The term "about" denotes that the thereafter following value is no exact value but is the center point of a range that is +/−5% of the value of the value. If the value is a relative value given in percentages the term "about" also denotes that the thereafter following value is no exact value but is the center point of a range that is +/−5% of the value, whereby the upper limit of the range cannot exceed a value of 100%.

Reference in the specification to "one embodiment" or "an embodiment" means that a particular feature, structure, or characteristic described in connection with the embodiment can be included in at least one embodiment of the invention. The appearances of the phrase "in one embodiment" in various places in the specification do not necessarily all refer to the same embodiment.

Reference in the specification to "local annotation(s)" means metadata (e.g., text, marking, number, and/or another type of metadata) that applies to part of an image, and not to the image as a whole. For example, in one embodiment, a local annotation can be a marking of a region of interest in an image, such as a histology image. Exemplary local annotations include markings outlining or otherwise identifying a portion of the image, e.g., a tumor region of the image, a stromal region of the image, identification of cell types within the image, identification of biological structures composed of multiple cells in the image, etc. In contrast, reference in the specification to "global annotation(s)" means metadata applied to the image as a whole. Exemplary global annotations include a label identifying the image as a whole, data regarding how the image was acquired, a label identifying a feature of the subject from whom the image is derived, e.g., a label indicating the age, sex, diagnosis, etc. of the subject from whom the image is derived, and/or any other data applying to the image as a whole. In some embodiments, a global annotation can indicate the presence, type, grade, or stage of a tumor known or understood to be present in the subject from whom the image is derived. In other embodiments, a global annotation can indicate a known characteristic of the subject from whom the image is derived, such as duration of survival (e.g., duration of survival following acquisition of the sample represented in the image) or response to a given treatment. In some embodiments described herein, images may be used that contain global annotations, in the absence of local annotations.

Reference in the specification to a "tile" means a subsection of an image.

The preceding detailed descriptions are presented in terms of algorithms and symbolic representations of operations on data bits within a computer memory. These algorithmic descriptions and representations are the tools used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be kept in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "segmenting," "tiling," "receiving," "computing," "extracting," "processing," "applying," "augmenting," "normalizing," "pre-training," "sorting," "selecting," "aggregating," "sorting," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Malignant mesothelioma (MM) is a rare cancer occurring in the lining of serous cavities that is often associated with asbestos exposure. Currently, a diagnosis of mesothelioma is made by a pathologist based on histological criteria established by the World Health Organization (WHO) in 2015. The WHO classification defines histological features that are used to classify a subject into one of three subtypes: epithelioid MM (EMM), sarcomatoid MM (SMM), or biphasic MM (BMM), which contains a mixture of both sarcomatoid and epithelioid components. EMM patients have the most favorable prognosis, with a median survival of 16 months, followed by BMM and then SMM patients, who have the worst prognosis, with a median survival of five months. The histological classification of a subject as EMM, SMM, or BMM currently serves as the best practice for predicting patient outcome, and is used to select the course of treatment for the subject. Notwithstanding, the predictive performance of the current classification criteria is sub-optimal in many cases, impacting the selection of appropriate treatment protocols.

The approach described herein based on deep convolutional neural networks (CNNs) can predict the overall survival of mesothelioma patients with greater accuracy than the traditional histological classifications of EMM, SMM, or BMM. The use of this approach has identified novel histopathological features that closely correlate with mesothelioma prognosis.

Traditionally, mesothelioma histopathology image analysis often relied on local annotation of regions of significance within the image by an expert pathologist, which is slow, laborious, and expensive, and thus is not well suited to high-throughput applications. In order to overcome this problem, an image processing pipeline can be used to analyze a mesothelioma histopathology image without the use of local annotations. This pipeline is initially based on segmenting a large image (e.g. WSI) into smaller images, e.g., 224×224 pixel images, and detecting a region of interest within the image on which to perform classification with Otsu's method. Thus, this classification works on small images, which are far less computationally expensive than a single large image. These smaller images are fed to a ResNet-type convolutional neural network to extract a feature vector from each small image, where the feature vector comprises local descriptors for that small image. A score is computed for each small image from the extracted feature vectors, as a local tile level (instance) descriptor. The top and bottom instances are used as input to a Multi-Layer Perceptron (MLP) to perform classification on them. This pipeline approach can provide good results, but its overall efficiency may still be improved.

A method and apparatus of a device that improves upon the above pipeline and classifies an image is described. In one embodiment, the device classifies a mesothelioma histology image using one or more neural network models to determine a label for that image. In this embodiment, the mesothelioma histology image can be a large image, where it is computationally impractical to process the image as a whole solely using a neural network model. In particular, the device reduces the amount of computing resources (e.g., time and/or memory requirements) needed to perform the image classification task on these large images. Such a reduction of resources further improves the performance of the device when executing the image classification task. In addition, the device can classify a whole-slide image, even when this type of image is too large to fit in the memory of a graphics processing unit commonly used to train machine learning models. In a further embodiment, the device reduces the dimensionality of the data, thus giving better generalization error and is more efficient in terms of model accuracy.

According to one embodiment, the device classifies at least one mesothelioma histology input image by segmenting the image between at least one region of interest containing information useful for classification and at least one background region containing little or no information useful for classification, by applying a first convolutional neural network. The device further tiles this region of interest of the image into a set of tiles. In addition, the device extracts a feature vector for each tile by applying a second convolutional neural network, where the features are local descriptors of the tile. Furthermore, the device processes the extracted feature vectors of the tiles in order to classify the image. In one embodiment, by segmenting the input image, the device processes a reduced number of tiles and avoids a processing of the whole image.

In one embodiment, the first convolutional network is a semantic segmentation neural network classifying the pixels of the input image as one of the following two categories: (a) Region of interest; and (b) Background region. Further, the tiling step (b) can be performed by applying a fixed tiling grid to the image, so that said tiles have a predetermined size. In addition, at least one level of zoom can be applied to the tiles. For example and in one embodiment, multiple levels of zoom can be applied to the tiles and tiles at different levels of zoom are combined. In addition, the device can optionally randomly sample the tiles and/or pad the set of tiles with blank tiles, so that the set of tiles comprises a given number of tiles.

In a further embodiment, the second convolutional neural network can be a residual neural network, such as a ResNet50 residual neural network or a ResNet101 residual neural network with the last layer removed using the previous layer as output, or a VGG neural network. This second convolutional neural network can be a pre-trained neural network, allowing the use of a state-of-the-art advanced neural network, without needing to have a large-scale image database and the computational resources to train this neural network.

In one embodiment, the device can compute at least one score of the tile from the extracted feature vector, where the tile score is representative of a contribution of the tile into the classification of the image. With the tile scores, the device can sort the set of the tile scores and select a subset of the tile scores based on their value and/or their rank in the sorted set; and applying a classifier to the kept tile scores in order to classify the image. The device can further apply this classification to multiple input images, where the device can aggregate groups of corresponding tiles from the different input images.

In an alternative embodiment, the device can also aggregate clusters of neighboring tiles. In this embodiment, aggregating a cluster of tiles can include concatenating the tiles of the cluster, selecting a single tile from the cluster according to a given criterion, using the cluster as a multi-dimensional object, or aggregating the values for example through a mean or a max pooling operation. In addition, the device can apply an autoencoder on the extracted feature vectors so as to reduce the dimensionality of the features. In one embodiment, the image can be a histopathology slide, the region of interest being a tissue region, and the classification of the image being a diagnosis classification.

In an alternative embodiment, when local annotations are available, such as the presence of tumors in regions of the slides, a hybrid technique can be used to take those annotations into account. To do so, the device can train the machine learning model for two concurrent tasks: (1) the local prediction of the presence of tumors and/or other macroscopic properties on each tile and the prediction of a set of global labels. A complex architecture can be used by the device (or multiple devices) that involves, on one side, the classification system described above, to process a set of 128 features. On the other side, the device applies a convolutional neural network to transform the features of the N tiles into an N*128 features vector. Based on this vector, the device trains a convolutional neural network to predict, for each tile, the presence or absence of tumor (or some other macroscopic property). The device can take both the output of the prediction and the N*128 features vector and apply an operation of weighted pooling on the concatenation of those two vectors to get a 128 features vector for the input image. The device concatenates the classification model's output and the 128 features obtained and try to predict based on this vector, a set of global labels for that image (e.g., survival, tumor size, necrosis, and/or other types of predictions). The loss of the model involves both global and local predictions. In this embodiment, by adding information derived from the local annotations into the computational flow, the performance of the overall model can be increased.

(A) Using a Classification Model to Determine the Prognosis of a Mesothelioma Subject FIG. 1 is a block diagram of one embodiment of a system for classifying a mesothelioma histopathology image by preprocessing and classifying the image using preprocessing and classification models. In FIG. 1, the system 100 includes a client 118 that is coupled to a preprocessing device 102, which is coupled to a classifying device 108. In one embodiment, the preprocessing device 102 and classifying device 108 receive the input image and output an image classification using the preprocessing model(s) 106 and classifying model(s) 112. In this embodiment, the image classification can be one of different labels, a number selected from a range of numbers, and/or other types of classification.

In one embodiment, each of the client 118, the preprocessing device 102, and classifying device 108 can be a personal computer, laptop, server, mobile device (e.g., smartphone, laptop, personal digital assistant, music playing device, gaming device, etc.), and/or any device capable processing an image. In one embodiment, the client 118, preprocessing device 102, and/or classifying device 108 can each independently be a physical or virtual device. In one embodiment, the client 118 can be a device used by a user to determine a classification for the image, such as a medical professional that wishes to determine a prognosis for a patient from the image. In one embodiment, the image can be a large image that is in the order of gigabytes. For example and in one embodiment, the image can be a digital image of a mesothelioma histopathology slide (e.g., WSI), where the image can be of the order of a few gigabytes or greater.

In a further embodiment, preprocessing device 102 segments the image into a region of interest and a background region. In this embodiment, by extracting a region of interest from the input image can decrease the amount of computation needed to classify the input image. For example and in one embodiment, histopathology slides (or other types of images) can include empty region(s) of the image with little or no tissue at all, thus it is useful to introduce what is called a "tissue detection" or "matter detection" method in order to evaluate if a region of the slide contains any tissue. More generally, when the goal is to classify a large image, it is relevant to identify regions of interest in the image and differentiate them from background regions. These regions of interest are the regions of an image containing valuable information for the classification process. In addition, the background regions are areas of the image that include little or no valuable information, where the background regions could be considered as noise for the task at hand. Image segmentation is further described in FIG. 2 below.

In one embodiment, with a segment image, the preprocessing device 102 can tile the image. In this embodiment, tiling is the process of partitioning the image into a group of image subsets. The image subsets can be of a fixed size or can be of varying sizes. In addition, the tiling can be based on the region of interest that is generated from the image segmentation described above. Tiling is further described in FIG. 2 below.

In a further embodiment, the preprocessing device 102 determines the features of the mesothelioma histopathology image using a convolutional neural network. In this embodiment, the preprocessing device 102 computes a feature vector for each tile is the set of tiles. These feature vectors can be used to classify the image by a classifier. Determining the features is further described in FIG. 2 below. In one embodiment, the preprocessing device 102 includes a preprocessing module 104 to perform the functionality of the preprocessing device 102 using one or more the preprocessing models 106.

In one embodiment, the preprocessing device 102 can send the tile set and the feature vectors to the classifying device 108, where the classifying device 108 classifies the input image 114 using the tile set, feature vectors, and a classifying model 112. In this embodiment, the classifying device 108 computes a tile score for each of the tiles in the set of tile, sorts the tile set and selects a subset of tiles from the tile set. With the tile subset, the classifying device 112 classifies the image from the subset of tiles and outputs the image classification 114. In one embodiment, the image classification is sent to the client 118. In alternative embodiments, the image classification 114 (and possibly along with the input image) can be stored in a repository, where the client can retrieve the input image 116 and/or image classification 114. Classifying the image using the tiles is further described in FIG. 2 below. In one embodiment, the functionalities of either the preprocessing device 102 or the classifying device 108 can be performed by the other device or alternatively, one device can perform the functionalities of the preprocessing device 102 and the classifying device 108. In one embodiment, the classifying device 108 includes a classifying module 110 to perform the functionality of the classifying device 108 using one or more the classifying models 112.

As described in FIG. 1, a client uses the preprocessing device 102 and/or classifying device 108 to preprocess and classify an image. In one embodiment, each of the preprocessing model 106 and/or classifying model 112 can be trained using a set of input mesothelioma histopathology images that have known properties. For example and in one embodiment, the classification model 112 can be trained using a set of input mesothelioma histopathology images and a set of known survival lengths for each of the input images. Furthermore, the set of input images may also include other information that can be used to train the image segmentation model.

Figure 2:
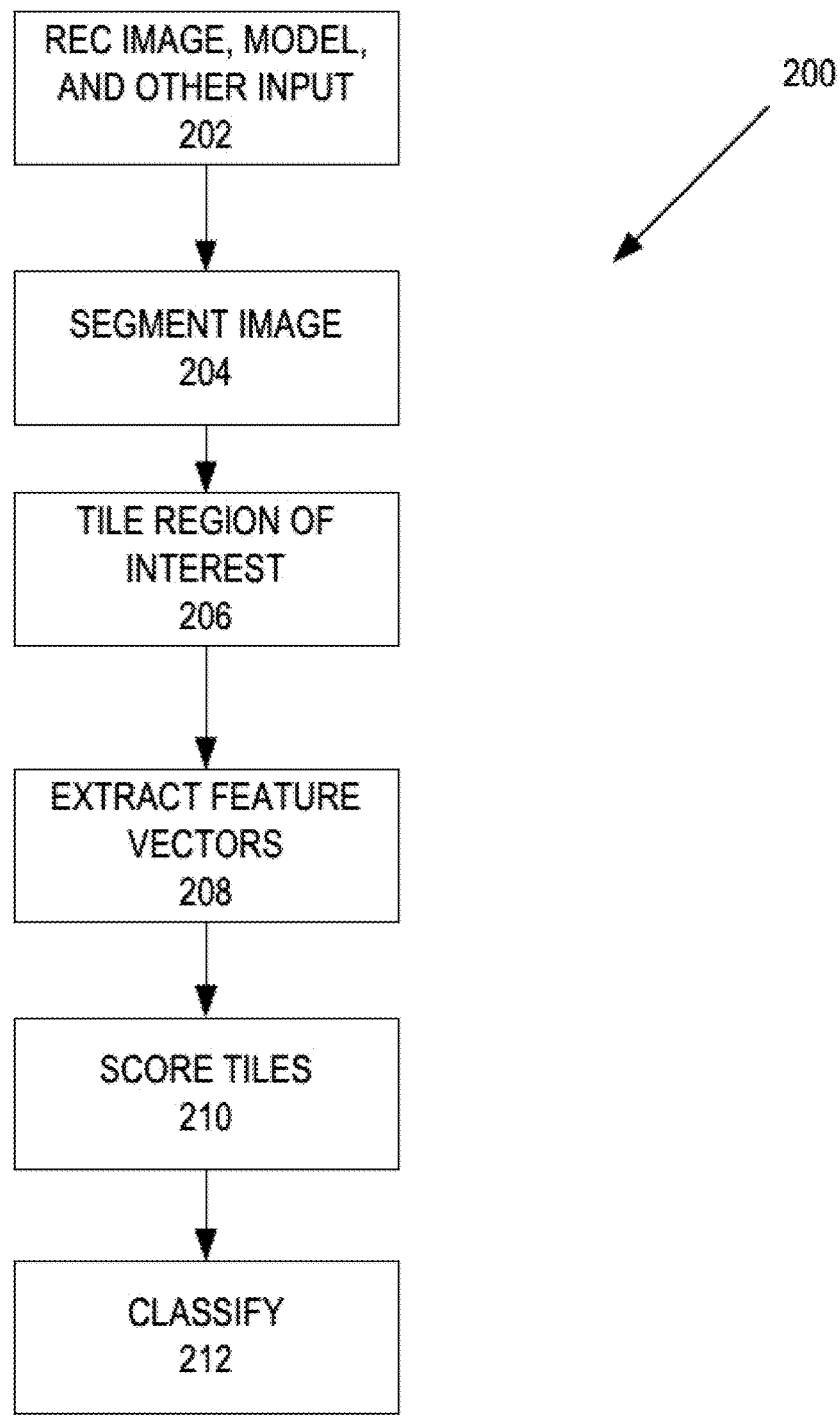
FIG. 2 is a flow diagram of one embodiment of a process to preprocess and to classify a mesothelioma histopathology image.

As per above, the preprocessing model 102 and classifying device 108 can preprocess and classify a mesothelioma histopathology image. FIG. 2 is flow diagram of one embodiment of a process 200 to preprocess and classify a mesothelioma histopathology image. In one embodiment, either the preprocessing device 102 and/or classifying device performs the functionalities of process 200. In FIG. 2, process 200 begins by receiving the mesothelioma histopathology image, the model(s), and other input at block 202. In this embodiment, the model is one or more models that can be used to preprocess and/or classify a mesothelioma histopathology image. For example and in one embodiment, the model can include an image segmentation model that is used segment the image, a feature extraction model, and a classification model that is used to classify the image. Furthermore, other input can include the weights and other input parameters used by process 200.

At block 204, process 200 segments that input image. In one embodiment, process 200 segments the input image into a region of interest and a background region. In this embodiment, by segmenting an image, process 200 can extract the region of interest for the input image. In this embodiment, extracting the region of interest from the input image can decrease the amount of computation needed to classify the input image. For example and in one embodiment, the mesothelioma histopathology slide can include empty region(s) of the image with little or no tissue at all. Thus, it is useful to introduce what is called a "tissue detection" or "matter detection" method in order to evaluate if a region of the slide contains any tissue. More generally, when the goal is to classify a large image, it is relevant to identify regions of interest in the image and differentiate them from background regions. This regions of interest is the regions of an image including valuable information for the classification process and background regions are areas of the image that include little or no valuable information, where the background regions could be considered as noise for the task at hand. In order to realize this task, various different types of image segmentation schemes can be used. For example and in one embodiment, Otsu's method can be used to segment the image, where Otsu's method is a simple thresholding method based on the intensity histogram of the image. In this embodiment, segmenting the image using Otsu's method has shown pretty good results when the image contains two classes of pixels following a bimodal distribution, for example foreground pixels and background pixels or, more specifically tissue and non-tissue. However, this method is known to perform badly on complex images when the histogram of intensity level cannot be assumed to have a bimodal distribution. This calls for a more robust technique in order to improve the overall efficiency of the method.

In another embodiment, and in order to improve the robustness of the image segmentation and to be able to tackle complex images (such as mesothelioma histopathology images), a semantic segmentation neural network can be used to segment the images, such as a U-NET semantic segmentation neural network, a SegNet, a DeepLab or another type of semantic segmentation neural network. In this embodiment, a semantic segmentation neural network can be used that does not depend on a particular distribution in the intensity histogram. Moreover, using such a neural network allows the image segmentation to take into account multichannel images such as Red-Green-Blue (RGB) images. Thus, the segmentation does not just rely on the histogram of pixel intensity but can take advantage of the semantics of the image. In one embodiment, the semantic segmentation neural network is trained to segment the tissue of the mesothelioma histopathology image from the background of this image, so as to differentiate a stained or unstained tissue from a background.

In a further embodiment, the original image can be downsampled in order to make the image segmentation step less computationally expensive. As will be described further below and in one embodiment, some of the image analysis is performed at a tile level (which is a subsection of the image), using the semantic segmentation on a downsampled version of the image does not degrade the quality of the segmentation. This allows the use of downsampled image without degrading the quality of the segmentation. In one embodiment, to obtain the segmentation mask for the original full resolution image, process 200 simply needs to upscale the segmentation mask generated by the neural network.

In another embodiment, another advantage of using a U-NET segmentation neural network is that this network type has been developed for biomedical image segmentation and thus, complies with the usual constraint of biomedical data, which is having small datasets of very high dimensionality. Indeed, the U-NET segmentation neural network is a model that has few parameters to train, making it possible to train this network with a fewer training examples. Moreover and in another embodiment, using data augmentation techniques on the training data can yield very good results with this architecture allowing to get more training examples from the same training sets.

Process 200 tiles the image into a set of image tiles at block 206. In one embodiment, process 200 uses the tiling increase the ability of preprocessing the images. For example and in one embodiment, using a tiling method is helpful in histopathology analysis, due to the large size of the whole-slide image. More broadly, when working with specialized images, such as histopathology slides, the resolution of the image sensor used in these fields can grow as quickly as the capacity of random-access memory associated with the sensor. With this increased image size, it is difficult to store batches of images, or sometimes even a single image, inside the random-access memory of a computer. This difficulty is compounded if trying to store these large images in specialized memory of a Graphics Processing Unit (GPU). This situation makes it computationally intractable to process an image slide, or any other image of similar size, in its entirety.

In one embodiment, by process 200 tiling the image (or region of interest) addresses this challenge by dividing the original image (or region of interest), into small images that are easier to manage, called tiles. In one embodiment, the tiling operation is performed by applying a fixed grid to the whole-slide image and using the segmentation mask generated by the segmentation method, selecting the tiles that include the tissue, or any other kind of region of interest for the later classification process. In order to reduce the number of tiles to process even further, an additional selection method can be used, such as random subsampling to keep a given number of slides.

For example and in one embodiment, process 200 divides the region of interest into tiles of fixed size (e.g., each tile having a size of 224×224 pixels). Alternatively, the tile size can be smaller or larger. In this example, the number of tiles generated depends on the size of the matter detected and can vary from a few hundred tiles to 50,000 or more tiles. In one embodiment, the number of tiles is limited to a fixed number that can be set based on at least the computation time and memory requirements (e.g., 10,000 tiles).

Additionally, process 200 can apply a zoom level to the tiles generated by the grid, where the zooming operation being adapted so that every tile has the same dimensions. The choice of the zoom is a trade-off between details and context: having a higher zoom level allows process 200 to extract more detailed information in a tile, whereas having a lower zoom level keeps the context of a selected area. To benefit from multiple levels of zoom, process 200 can extract tiles at multiple levels of zoom, making the model able to extract more information from a given slide. These multiple levels of zoom can be combined by concatenating multiple tiles at different zoom levels having the same center location.

At block 208, process 200 extracts feature vectors from the tile set. In one embodiment, feature extraction aims at building derived values, intended to be informative and non-redundant, facilitating the subsequent learning and generalization steps, from the tiles created from the input image. In one embodiment, the extracted features are in the form of numeric vectors also called local descriptors.

In one embodiment, process 200 can use any feature extraction neural network, such as a ResNet based architecture (ResNet-50, ResNet-101, ResNetX etc.), Visual Geometry Group (VGG) neural network, Inception neural network, an autoencoder for unsupervised feature extraction, a custom-made neural network, specifically designed for the task, or even non neural network feature extractors such as SIFT or CellProfiler. Moreover, the feature extraction neural network used can be a pre-trained one as these are trained on very large-scale datasets, and thus have an optimal generalization accuracy.

In one embodiment, process 200 uses a ResNet-50 neural network as this neural network can provide well suited features for image analysis without requiring too much computing resources. For example and in one embodiment, the ResNet-50 can be used for mesothelioma histopathological image analysis. In this example, the ResNet-50 neural network relies on residual blocks that allow the neural network to be deeper and still improve its accuracy, as simple convolutional neural network architectures can get worst accuracies when the number of layers grows too large. In one embodiment, the weights of the ResNet-50 neural network can be the weights used for the feature extraction are from a pre-training on the dataset ImageNet, since this dataset is a really general-purpose image dataset. In one embodiment, using a neural network pre-trained on a large independent image data set provides good features independently of the kind of images, even in the case where the input images are specialized, as is for histopathological images (or other types of images). In this embodiment, process 200 uses ResNet-50 convolutional neural network to extract 2,048 features per tile. If process 200 extracts 10,000 tiles, for example, process 200 generates a matrix of 2,048×10,000. Furthermore, if process 200 is being executed with a number of images as input then process 200 generates a tensor with dimensions of: number of images×number of features/tile× number of tiles.

Process 200, in one embodiment and in order to extract features for a given slide, processes each of the selected tiles goes through the ResNet-50 neural network outputting the feature vector for that tile. In this embodiment, the feature vector can be a vector of dimensional 2048 or another size. In addition, process 200 can apply an autoencoder to the feature vectors to further provide dimensionality reduction (e.g., reducing the dimensions of the feature vectors to 256 or another dimensional). In one embodiment, the autoencoder can be used when the machine learning model may be susceptible to over fitting. For example and in one embodiment, process 200 can reduce the length of a 2,048 feature vector down to a 512 length feature vector. In this example, the process 200 uses the autoencoder, which includes a single hidden-layer architecture (of 512 neurons). This prevents the model from over-fitting by finding several singular features in the training dataset and also reduces computation time and required memory. In one embodiment, the classification model is trained on a small subset of the image tiles, e.g., trained on 200 tiles randomly selected from each slide (out of a total of 411,400 tiles).

Process 200 can optionally perform a zero-padding operation on the feature vectors, in order to derive a minimal number of features. In this embodiment, process 200 can perform a zero-padding to add feature vectors to the set of feature vectors for the image if the number of feature vectors is below a minimal number of feature vectors. In this embodiment, each zero-padded feature vector has null values.

Process 200 scores each of the tiles at block 210. In one embodiment, process 200 reduces each of the feature vectors to one or more scores using either a connected neural network. In one embodiment, process 200 can reduce the feature vector to a single score using a fully connected neural network, or to multiple scores representing various characteristics of the tile using one fully connected neural network outputting various scores or a plurality of fully connected neural networks, each outputting a different score. These scores, associated with one tile, are sorted and a subset of the tiles is selected for the image classification. In one embodiment, this subset of tiles can be tiles with the top R highest scores and the bottom R lowest scores, the top R highest scores, the bottom R lowest scores, and/or any weighted combination of the scores. Finally, these scores are concatenated into an image score vector that can be taken as input for the image classification.

For example and in one embodiment, process 200 can use a convolutional 1D layer to create a score for each tile. In this example, as described above with feature vectors of 2,048 length, this convolutional layer performs a weighted sum between the 2,048 features of the tile to obtain this score, where weights of this sum are learned by the model. Furthermore, because the convolutional 1D layer is unbiased, the zero-padding tiles have a score of zero and thus a reference for a totally uninformative tile. Process 200 picks the highest and lowest R scores and uses them as input for the classifying described below. This architecture ensures which tiles are used to make the predictions and therefore, how process 200 predicts the result. Tile scoring is further described in FIG. 3 below.

At block 212, process 200 classifies the image using the tile scores to predict one or more global labels for the image.

In one embodiment, process 200 uses the image score vector as input to a dense multilayer neural network to provide the desired classification. This classification can be any task that associates labels to the data given as input to the classifier. In one embodiment, using a trained classifier for mesothelioma histopathology image inputs since said input data is derived by the whole pipeline, the classifier is thus capable to label the mesothelioma histopathology image given as input without needing to process the full image, which can be computationally prohibitive. For example and in one embodiment, the labels can be a label of any kind, such as: binary values representing prognosis of a given pathology; numeric labels representing a score, a probability, or a prediction of a physical quantity, such as survival prediction or response to treatment prediction; and/or a scalar label as described previously or a vector, matrix or tensor of such labels representing structured information. For example and in one embodiment, process 200 can output a continuous risk score as the classification for mesothelioma histopathology input images, which can be used to determine an estimated survival duration of a subject. In this example, different continuous output scores for different subject that can be plotted against similar risk scores derived from a plurality of mesothelioma subjects of known survival duration, to determine an estimated survival time for the individual test subject. In one embodiment, process 200 uses a multi-layer perceptron (MLP) with two fully connected layers of 200 and 100 neurons with sigmoid activation. In this embodiment, the MLP is used as a core of the predictive algorithm that transforms the tile scores to label(s). While in one embodiment, process 200 predicts a single label for the image (e.g., a risk score), in alternate embodiments, process 200 can predict multiple global labels for the image. In one embodiment, process 200 can perform a multi-task learning environment to predict multiple global labels. For example and in one embodiment, the classification model (e.g., the MLP and/or other models described elsewhere) can be trained to predict multiple labels at once in the multi-task learning environment (e.g., survival or disease-free survival, and/or other predictions using the resulting feature vector (e.g., clinical data, tumor size, vascular invasion, necrosis, and/or other types of predictions).

Figure 3:
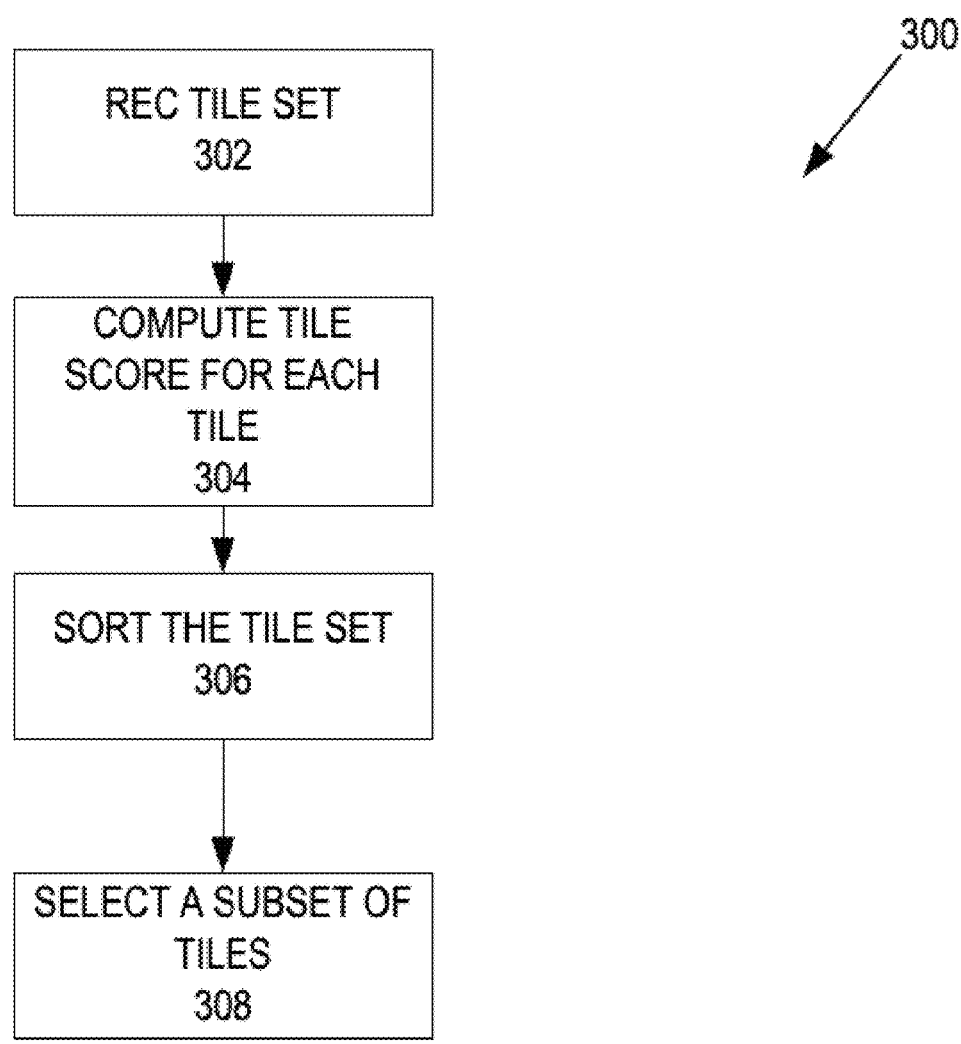
FIG. 3 is a flow diagram of one embodiment of a process to classify a mesothelioma histopathology image that is tiled into a set of tiles.

As can be seen from FIG. 2, the mesothelioma histopathology image can be classified based on at least a set of tile scores that are derived from the image tile feature vectors generated from the neural network. FIG. 3 is flow diagram of one embodiment of a process 300 to score a mesothelioma histopathology image that is tiled into a set of tiles. In one embodiment, a process, such as process 200 at block 210 performs process 300 to score the image. In FIG. 3, process 300 begins by receiving the tile set at block 302. In one embodiment, the tile set is the tile set that is generated in FIG. 2 at block 206. In addition, the tile set includes a feature vector for each tile in the tile set. At block 304, process 300 computes a tile score for each tile using the associated feature vector for that tile. For example and in one embodiment, process 300 can use a convolutional 1D layer to create a score for each tile. In the example described above with feature vectors of 2,048 length, this convolutional layer performs a weighted sum between all 2,048 features of the tile to obtain this score, where weights of this sum are learned by the model. Furthermore, because the convolutional 1D layer is unbiased, the zero-padding tiles have a score of zero and thus a reference for a totally uninformative tile.

At block 306, process 300 sorts the tile set. In one embodiment, process 300 sorts the tile set to determine the top R and/or bottom R scores for block 308 below. Process 300 selects a subset of tiles at block 308, where this subset of tiles is used for the classification step later on. In one embodiment, this subset of tiles can be tiles with the top $R_{top}$ highest scores and the bottom $R_{bottom}$ lowest scores, the top $R_{top}$ highest scores, the bottom $R_{bottom}$ lowest scores, and/or any weighted combination of the scores. In one embodiment, the ranges of values for $R_{top}$ and/or $R_{bottom}$ can be the same or different. In addition, the $R_{top}$ and/or $R_{bottom}$ ranges can be a static numerical range (e.g., 10, 20, 100, or some other number), adapted to a range, a percentage, a label (e.g., small, large, or some other label), set via a user interface component (slider, user input, and/or another type of user interface component), and/or some other value. In one embodiment, process 300 additionally concatenates these scores into an image score vector that can be taken as input for the image classification.

In one embodiment, when studying mesothelioma histopathology whole-slide images (or slides), a single patient can be associated with multiple slides, taken with various stainings, at various locations of the same sample, from multiple organs, or at various time points. In this embodiment, the slides from a single patient can be aggregated in multiple ways. In one embodiment, process 200 can concatenate the slides, in order to form a larger slide that will be processed in the same or similar way as a normal one (segmentation, tiling, feature extraction and classification).

In a further embodiment, process 200 can handle the multiple slides as a three-dimensional image. This can be particularly useful when the slides are multiple consecutive slices of the same tissue. In this case, a 3D Convolutional Neural Network (CNN) can be used for the feature extraction step in order to get the most information out of the given set of slides. Furthermore, by applying the segmentation, tiling and feature extraction steps to the plurality of slides and keeping only a given number of features so as to match the input dimensions of the classifier use, the features selected could be for example the N maximum features and M minimum features for each tile. This approach is particularly suitable in the case where the plurality of slides to be assembled is a batch of the same slide but using various stainings.

In another embodiment, process 300 can cluster the tiles that are close according to a distance metric computed on the image or on the features and aggregating their associated feature vectors by computing the mean, the maximum or a weighted sum of the feature vectors. This allows process 300 to reduce the dimensionality of the problem greatly by starting from a large number of tiles (for example 10,000 tiles) and aggregating them into a small number of clusters (for example 200), this decreases the computation time but also reduces overfitting and giving the models better generalization error. More particularly a good distance metric for selecting the tiles to aggregate is the Euclidean distance in the whole-slide image, for example aggregating all the tiles contained in a 1 mm$^2$ patch on the slide.

In another embodiment, a slide may not contain enough useful tissue to extract as tiles on which to apply the feature extraction step and thus to feed the classifier with features. In this case, the input of the classifier is zero padded, meaning that for every tile lacking, a feature consisting of zeros is added to the real features computed by the feature extractor.

Figure 4:
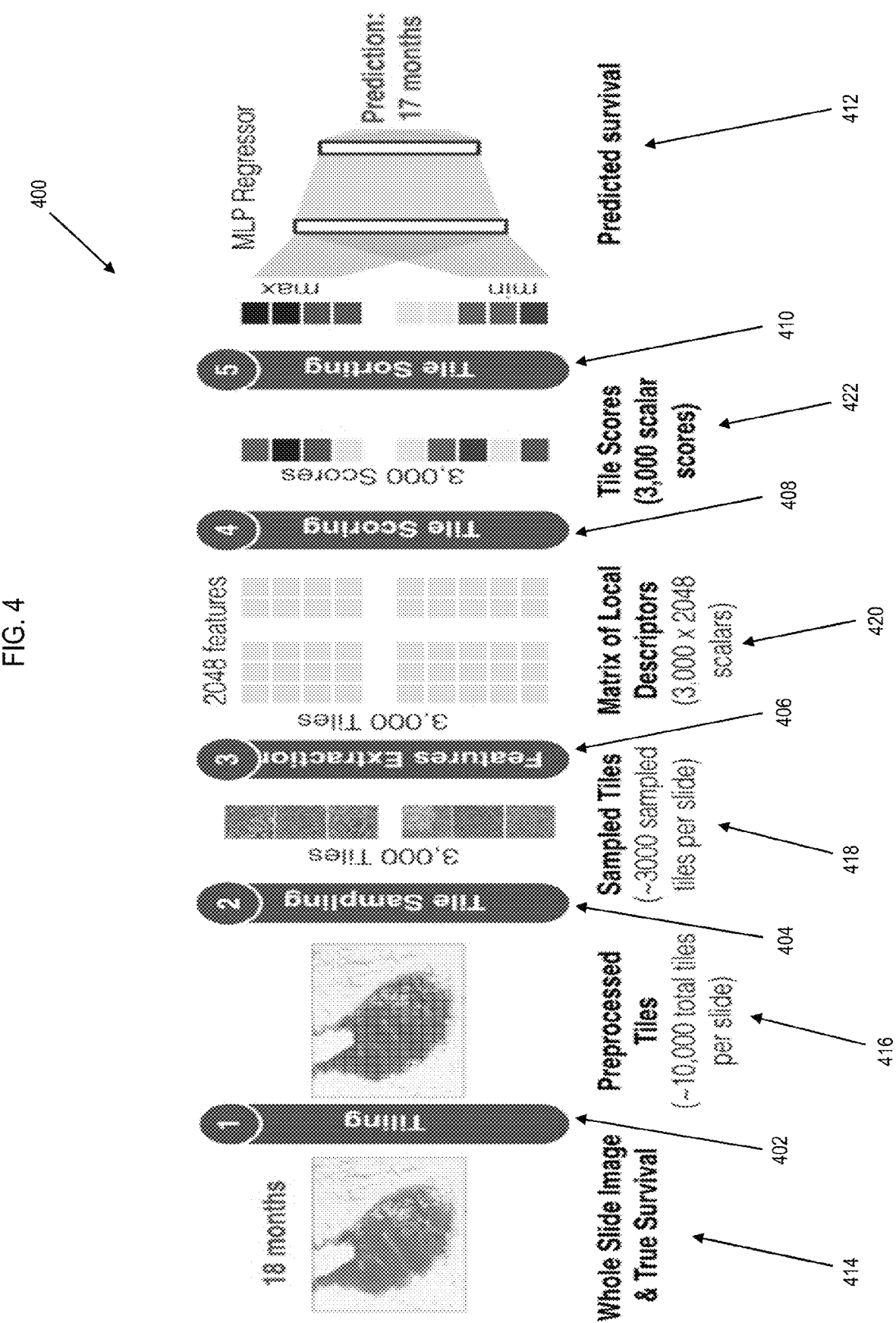
FIG. 4 depicts the layout of an exemplary embodiment of the MesoNet predictive model. The regression architecture is composed of five steps: 1. The "tiling" process divides a whole slide image into small tiles of 224×224 pixels. 2. The tiles are then randomly subsampled for computational purposes. 3. Features are then extracted from each tile using ResNet50. 4. A Convolutional 1D layer is used to score each tile. 5. Tiles associated with the largest and lowest scores are then retained to train a multilayer perceptron regressor to predict overall survival of the patient.

As described above, one example of the image classification is for classifications for mesothelioma histopathology images. In this example, the computed label is a prediction value for a patient based on an input mesothelioma histopathology slide image. FIG. 4 is an illustration of a classification system 400 for a mesothelioma histopathology image classification. In FIG. 4, the classification system 400 includes the functions of tiling 402, tile sampling 404, feature extraction 406, tile scoring 408, tile sorting 410, and classification (in this case, predicting survival) 412. In one embodiment, the tiling 402 function receives the whole slide image 414 and outputs a set of preprocessed tiles 416. In this embodiment, the number of tiles for the image can be on the order of 10,000 tiles. In further embodiment, there can be more or less number of tiles for the image. In one embodiment, and to reduce the computational complexity, the classification system 400 samples the tiles 404 to reduce the number of tiles 418 that are used in the neural network computations. In one embodiment, the classification system 400 samples the tiles 404 randomly or some other type of sampling mechanism. For example and in one embodiment, the classification system 400 randomly samples the tiles 404 to reduce the number of tiles from on the order of 10,000 tiles to on the order of a few thousand tiles (e.g., 3000 tiles).

In one embodiment, the classification system 400 performs a feature extraction 406 function on the sampled tiles. In this embodiment, the classification system 400 uses a convolutional neural network to extract the features on the sampled tiles that results in a matrix of local descriptors 420 (e.g., using a ResNet-50, or another type of feature extraction mechanism described above). Furthermore, and in one embodiment, the classification system 400 scores 422 the tiles based on at least the tile feature vectors 408. In this embodiment, the classification system 400 uses a 1D convolutional neural network to generate the scores for each of the image tiles. The classification system 400 additionally sorts the tiles scores 410, where the sorted tiles are used by a MLP regressor to generate a predicted survival 412.

In one embodiment, the selection of the tiles can be used by an investigator to determine correlations between the mesothelioma histopathology image features and relevant features in the images. In this embodiment, for a particular type of image, the investigator can review selected tiles from images with known (or unknown) labels to determine correlations. For example and in one embodiment, an investigator can review selected tiles from histopathology images processed by process 200 and compare the selected tiles with corresponding image labels or other corresponding data that indicate length of survival so as to discover or correlate trends between survival and histology image features indicated by the selected tiles.

Figure 5:
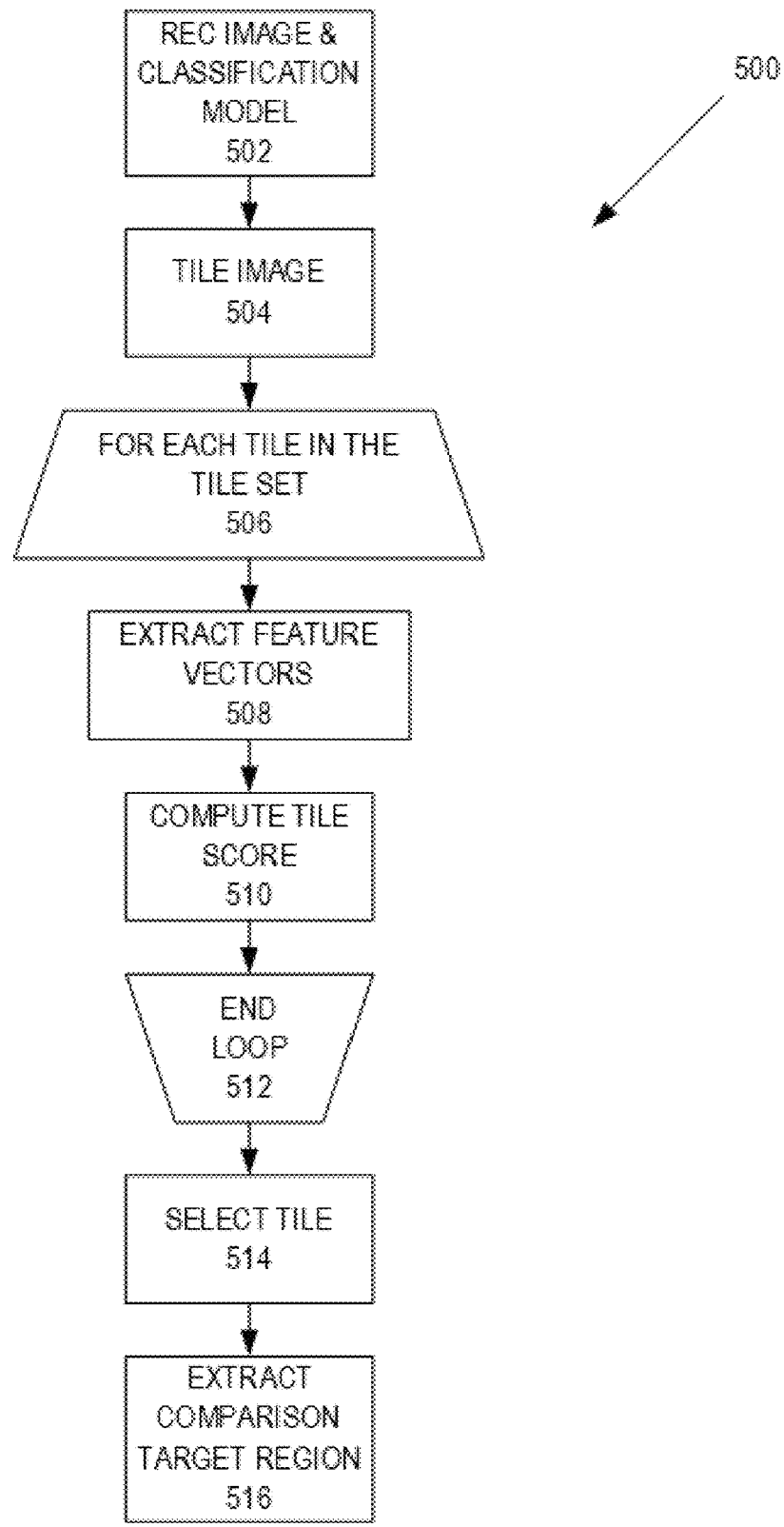
FIG. 5 is a flow diagram of one embodiment of a process to extract a comparison target region from a mesothelioma histopathology image.

In addition to predicting a label for an image as described in FIG. 1 above, the preprocessing device 102 and/or classifying device 108 can further extract a comparison target region for an image based on the tile scores for that image. In this embodiment, the comparison target region is different a region of interest as described in FIG. 2 because tiles in the comparison target region are similar to one or more of the tiles with the minimum or maximum scores. For example and in one embodiment, the comparison target region tiles can be tiles with average scores (or scores that are not the minimum or maximum scores) that resembles tiles from the maximum or minimum scored tiles. FIG. 5 is a flow diagram of one embodiment of a process 500 to extract a comparison target region from a mesothelioma histopathology image. In FIG. 5, process 500 begins by receives the image and the model(s) at block 502. In one embodiment, the models can include models used to segment the image, extract feature vectors, and/or score the feature vectors as described in FIG. 2 above. At block 504, process 500 segments the image. In one embodiment, process 500 segments the image as described in FIG. 2, block 204. Process 500 tiles the image at block 506. In one embodiment, process 500 tiles the image as described in FIG. 2, block 206. At block 508, process 500 extracts the feature vectors for the image. In one embodiment, process 500 extracts a feature vector for each of the image tiles as described in FIG. 2, block 205. Process 500 scores the image tiles using the extracted feature vectors at block 510. In one embodiment, process 500 scores the image tiles as described in FIG. 2, block 210. The processing loop ends at block 512.

At block 514, process 500 selects an image tile using at least the tile score. In one embodiment, this tile is used to determine the comparison target region. In one embodiment, process 500 select the tile based on at least the tile score and a rank of the tile score. In this embodiment, process 500 can select the top number ($R_{top}$) number and/or a bottom number ($R_{bottom}$) of scores. In one embodiment, $R_{top}$ and $R_{bottom}$ represent the top and lowest tiles scores. In one embodiment, the ranges of values for $R_{top}$ and/or $R_{bottom}$ can be the same or different. In addition, the $R_{top}$ and/or $R_{bottom}$ ranges can be a static numerical range (e.g., 10, 20, 100, or some other number), adapted to a range, a percentage, a label (e.g., small, large, or some other label), set via a user interface component (slider, user input, and/or another type of user interface component), and/or some other value. Alternatively, process 500 can select a set of one or more tiles that are either above a first threshold of a tile scores or below a second threshold tile score, where the first threshold can be the same or different. In a further embodiment, process 500 randomly selects one or more tiles based on at least a probability derived from at least a corresponding tile score.

Process 500 extracts a comparison target region at block 516. In one embodiment, process 500 uses the selected tile(s) from block 510 above to extract the comparison target region associated with the selected tile(s) having an average score and in visual proximity with at least one of the selected tiles according to a distance metric. For example and in one embodiment, the distance metric process 500 uses to evaluate the visual proximity between two tiles can be a L2 norm computed on the extracted features of the two tiles and/or a L2 norm computed on those two tiles.

As described above, the models used for classification and tile selection do not require or use local annotations of the images made by a specialist (e.g., a pathologist). In another embodiment, if there are local annotations present in the image, these local annotations can be used to improve the predictive use of the model(s). Thus, in one embodiment, when local annotations are available, such as the presence of tumors in regions of the slides, a hybrid technique can be used to take those annotations into account. To do so, a device can train the machine learning model for two concurrent tasks: (1) the local prediction of the presence of macroscopic properties on each tile (e.g., presence of tumors or other types of macroscopic properties) and the prediction of a set of global labels. A complex architecture can be used by the device (or multiple devices) that involves, on one side, the classification system described above in FIG. 2 to process a set of 128 features. On the other side, the device applies a convolutional neural network to transform the features of the N tiles into an N*128 features vector. Based on this vector, the device trains a convolutional neural network to predict, for each tile, the presence or absence of tumor. The device can take both the output of the prediction and the N*128 features vector and apply an operation of weighted pooling on the concatenation of those two vectors to get a 128 features vector for the input image. The device concatenates the classification model's output and the 128 features obtained and try to predict based on this vector, a set of global labels for that image (e.g., survival, tumor size, necrosis, and/or other types of predictions). The loss of the model involves both global and local predictions. In this embodiment, by adding information derived from the local annotations into the computational flow, the performance of the overall model can be increased.

Figure 6:
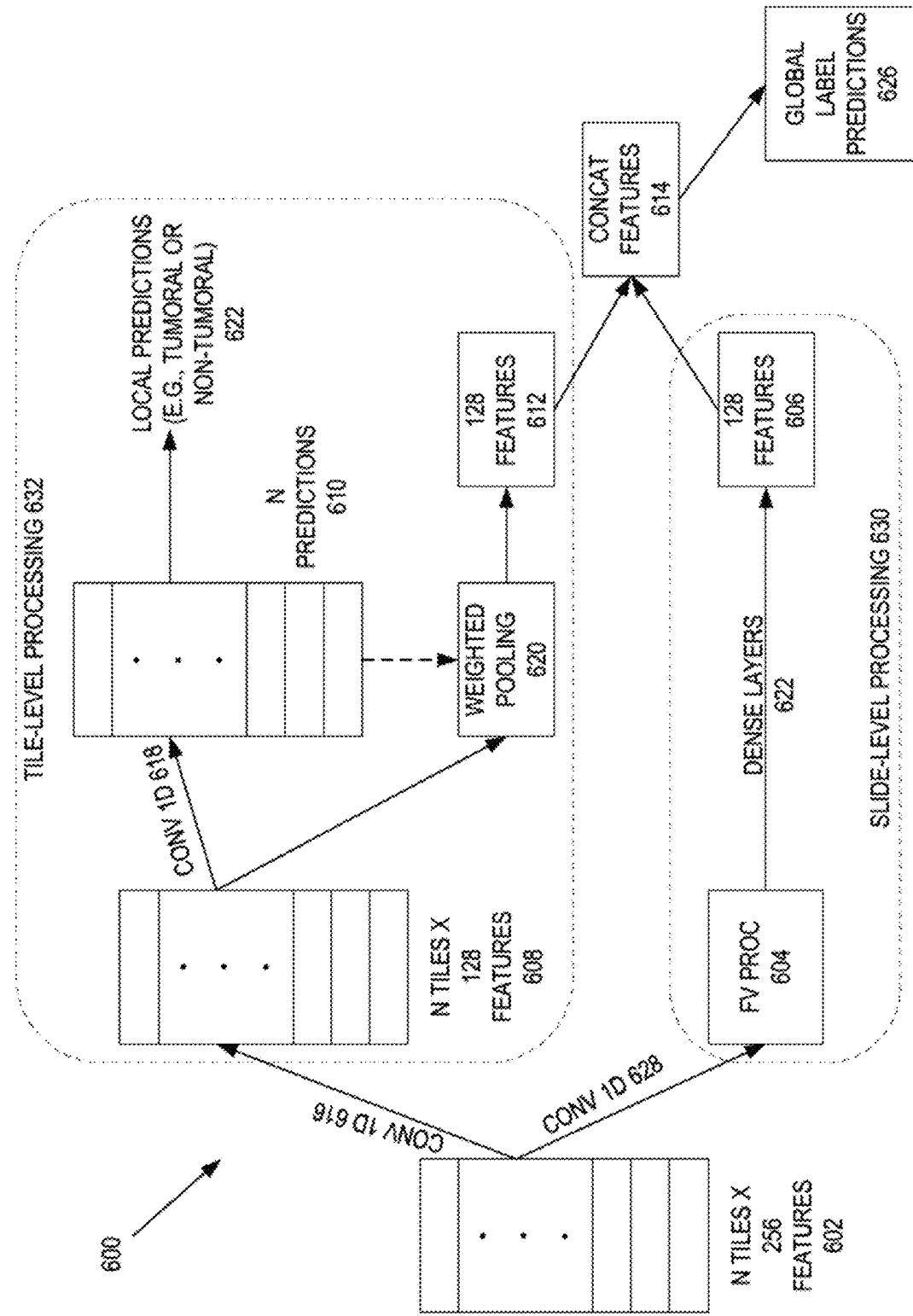
FIG. 6 is a block diagram of one embodiment of a system for classifying an image using a classification model and local annotations.

FIG. 6 is a block diagram of one embodiment of a system 600 for classifying an image using a classification model and local annotations. In FIG. 6, the system 600 can include both a slide-level processing 630 and a tile-level processing 632. In one embodiment, the slide-level processing 630 processes the tiles using the local annotations to improve the global label predictions of the overall system 600. In one embodiment, the tile-level processing 632 processes the tiles and feature vectors as described in FIG. 2 above. Furthermore, the results of each of the slide-level processing 630 and the tile-level processing 632 can be combined and further processed to determine various predictions that will be described below.

In one embodiment, the system 600 receives an image with a set of N tiles and a corresponding set of feature vectors that is derived from an input image using a tiling and feature vector generation operation. For example and in one embodiment, the system 600 receives a tiled image and corresponding set of feature vectors that is generated as described in FIG. 2 above. While in one embodiment, system 600 receives N tiles with a set of feature vectors of 256 features for each feature vector, in an alternative embodiment, the set of feature vectors can include feature vectors with a smaller or greater number of features. The system 600 further sends the set of feature vectors to the slide-level 630 and tile-level 632 processing. In this embodiment, each of the feature vectors for the slide-level processing 630 are reduced from 256 features to 128 features. In one embodiment, the feature vectors are reduced by using a one dimensional convolutional neural network 616. In this embodiment, this one dimensional convolutional neural network 616 is used to extract the interesting features for each tile. The one dimensional convolutional neural network 616 can be applied once, multiple times, or none at all. While in one embodiment, the number of features per feature vector is reduced by one half, in alternate embodiments, the number of features vector can remain the same, decrease by a different amount, and/or increase. In a further embodiment, the system 600 sends the set of feature vectors to the slide-level processing 630 after applying a one dimensional convolutional neural network 628 is used to extract the interesting features for each tile.

In one embodiment, the tile-level processing 632 begins by receiving the set of feature vectors 608 that is generated by the one dimensional convolutional neural network 616 described above. The tile-level processing 632 further trains a second one dimensional convolutional neural network to the set of feature vectors 608 using the local annotations. In this embodiment, second one dimensional convolutional neural network can then be used to predict the presence of macroscopic features 610 in each of the tiles for an input image that does not include any local annotations (e.g., the presence or not of tumors in each tile, the presence of other macroscopic medical features (e.g., inflammation, etc.), and/or the presence of other types of features). If there are local annotations for some or all of the tiles, the N predictions can be supplemented or replaced with predictions derived from the available local annotations. For example and in one embodiment, if a pathologist determines a partial or full outline or identification of a tumor on the image, the N predictions for the corresponding N tiles can be derived from the indication or absence of tumors for each image tile. If there are not any local annotations, can use this trained one dimensional convolutional neural network to create the N predictions. These N predictions 610 can be combined with the convolved features vector set 608 to create a new feature vector 612 by a weighted polling of the N predictions and the convolved features vector set 608. In one embodiment, the new feature vector 612 is 128 features. In this embodiment, the weighted pooling is used to weight the N predictions with the feature vector set 608. In an alternative embodiment, the new feature vector 612 can have more or less features.

Concurrently, the slide-level processing 630 receives the original feature vector set 602 and performs the feature vector processing as described in FIG. 2 above using dense layers 622 to generate a feature set 606. While in one embodiment, the feature vector set 606 is 128 features, in alternate embodiments, the feature vector set 606 can include more or less numbers of features.

In one embodiment, with the feature vector 606 generated by the slide-level processing 630 and the feature vector 612 generated by the tile-level processing 632, the system has two different feature vectors. The system can additionally combine these feature vectors by concatenating the two feature vectors into a resulting feature vector 614, where the resulting feature vector 614 can be used to predict one or more global labels 928. For example and in one embodiment, one or more global labels can be predicted for medical image slide, such, such as survival or disease-free survival, clinical data, tumor size, vascular invasion, necrosis, and/or other types of predictions. In one embodiment, by using the feature vectors from both the slide-level processing 630 and the tile-level processing 632, the resulting feature vector 614 can have an influence from the local annotations, which then can be used for predictions.

Figure 7:
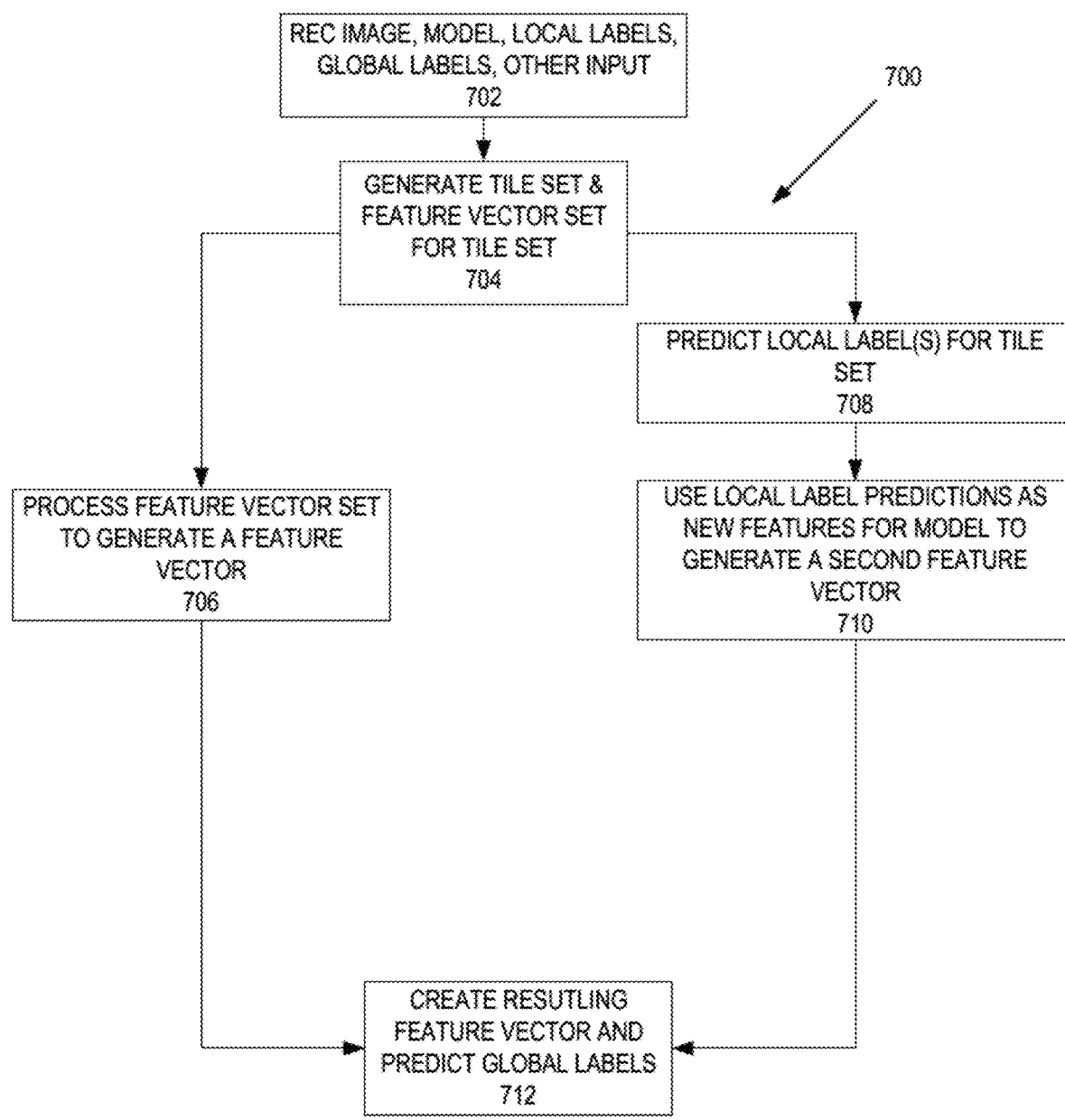
FIG. 7 is a flow diagram of one embodiment of a process to classify an image using a classification model and local annotations.

As per above, the system 600 can use local annotations, if available, to further improve the predictive abilities of the classification model(s). FIG. 7 is a flow diagram of one embodiment of a process 700 to classify an image using a classification model and local annotations. In FIG. 7, process 700 begins by receiving the image, the local annotations, and the global label at block 702. In one embodiment, the local annotations can be data and/or metadata that can describe and/or indicate the presence or lack thereof macroscopic features in the input image. For example and in one embodiment, the local annotations can indicate certain regions of the image has a tumor or tumor-like tissue. At block 704, process 700 tiles the image and generates a set of feature vectors. In one embodiment, process 700 generates a feature vector for each of the tiles in the image. In this embodiment, each of the feature vectors can include 256 features. For example and in one embodiment, process 700 tiles and generates the feature vector as described in FIG. 2 above.

At this point, the process 700 can take two paths for the slide-level and tile-level processing. For the tile-level processing, at block 706, process 700 applies the classification model(s) to generate a feature vector of 128 features. In one embodiment, process 700 applies the classification model(s) to the set of feature vectors as described in FIG. 2, block 208. Execution proceeds to block 712 below.

Process 700 performs the slide-level processing starting at block 708. At block 708, process 700 predicts the local label for each of the image tiles. In one embodiment, process 700 applies a one dimensional convolutional neural network to extract the interesting features of the set of the 256 features vectors. In addition process 700 can train a second convolutional neural network using the local annotations to generate a set of predictions for each of the tiles. Alternatively, process 700 can the set of predictions from the input local annotations. Process 700 uses the local predictions as the features for the model at block 710. At this point, process 700 has generated a feature vector of 128 features from the slide-level processing of bocks 708 and 710. Execution proceeds to block 712 below.

At block 712, process 700 combines the features from blocks 706 and 710 to create a resultant feature vector of 256 features. In one embodiment, process 700 creates the resultant feature vector by concatenating the two feature vectors from blocks 706 and 710. Alternatively, the resultant features vector can be created using alternative means. In addition, at block 712, process 700 predicts global labels (e.g., for a medical image slide, such as survival or disease-free survival, clinical data, tumor size, vascular invasion, necrosis, and/or other types of predictions). In one embodiment, process 700 predicts the global labels by scoring the tiles and creating the predictions as described in FIG. 2, blocks 210 and 212 above.

(B) Histopathological Features Indicative of Mesothelioma Prognosis

Unlike traditional black-box deep learning methods, the classification models described herein can identify regions of a mesothelioma image that contribute to the prognosis. Images of greatest significance to the prognosis of a subject can be identified by, for example, selection of a cohort of tiles having highest and lowest R scores. The highest and lowest cohorts of tiles identified by the model as having the best correlation with a given endpoint, e.g., duration of survival, can be analyzed by a pathologist to determine features within the tiles that have prognostic significance. For example, in some embodiments, features associated with the duration of survival of a subject can be determined by analysis of the cohort of tiles having R scores in the top 20%, e.g., top 15%, top 10%, top 5%, top 2%, top 1%, etc., and/or in the bottom 20%, e.g., bottom 15%, bottom 10%, bottom 5%, bottom 2%, bottom 1%, etc. of all of the tiles assessed by the model.

Mesothelioma features associated with a prognosis of low survival duration include one or more of the following, and combinations thereof (also referred to herein as "low survival features"):

a. presence and/or elevated number of pleomorphic and/or atypical cells in a stromal region adjacent to a tumor region
b. presence and/or elevated number of pleomorphic and/or atypical cells in a tumor region;
c. reduced inflammatory response, evidenced by e.g., reduced inflammation and/or reduced numbers of inflammatory cells;
d. a transitional histopathological pattern;
e. higher grade (e.g., grade 3) cellular morphology with atypical nuclei;
f. poorly vascularized tumor and/or stromal region;
g. stromal response pattern comprising cancer-associated fibroblasts with small vessels unevenly distributed together with inflammatory cells;
h. areas of vacuolated and atypical cells in a dense collagenous stromal region
i. increased number of cells having a spindle or transitional shape;
j. presence of sarcomatoid components;
k. absence of epithelioid components;
l. presence of discohesive cells having loosened or reduced intercellular connections.

In some embodiments, a mesothelioma image weighing toward a prognosis of low survival duration contains one or more, two or more, three or more, four or more, five or more, six or more, seven or more, eight or more, nine or more, ten or more, eleven or more, or twelve or more of the foregoing low survival features. In some embodiments, the mesothelioma image is a whole slide image. In other embodiments, the mesothelioma image is a section of a whole slide image, e.g., a tile derived from a whole slide image.

Histological features most commonly found in tiles predictive of low survival include higher grade, presence of pleomorphic cells, atypia, spindle or transitional shaped cells, presence of discohesive cells, presence of sarcomatoid features, and/or vacuolization.

Mesothelioma features associated with a prognosis of high survival duration include one or more of the following, and combinations thereof (also referred to herein as "high survival features"):

a. absence and/or reduced number of pleomorphic and/or atypical cells in a stromal region adjacent to a tumor region;
b. absence and/or reduced number of pleomorphic and/or atypical cells in a tumor region;
c. increased inflammatory response, evidenced by e.g., increased inflammation and/or increased numbers of inflammatory cells;
d. tubular architecture;
e. lower grade (e.g., grade 1 and/or grade 2) cellular morphology with typical nuclei;
f. well-vascularized tumor and/or stromal region;
g. absence of areas of vacuolated and atypical cells;
h. absence of cells having a spindle or transitional shape;
i. presence of epithelioid components;
j. absence of sarcomatoid components;
k. absence of discohesive cells having loosened or reduced intercellular connections.

In some embodiments, a mesothelioma image weighing toward a prognosis of high survival duration contains one or more, two or more, three or more, four or more, five or more, six or more, seven or more, eight or more, nine or more, ten or more, or eleven or more of the foregoing high survival features. In some embodiments, the mesothelioma image is a whole slide image. In other embodiments, the mesothelioma image is a section of a whole slide image, e.g., a tile derived from a whole slide image.

Histological features most commonly found in tiles predictive of high survival include presence of inflammatory response, fibromyxoid stroma, fibrosis, papillary morphology, presence of vascularization, low grade, lymphocytic cells, presence of vessels, stromal involvement, and tubule-papillar morphology.

The features identified herein as predictive of low survival and/or high survival can be used to determine the prognosis of a subject known or suspected of having mesothelioma.

The presence or absence of any one or more of the low survival features and/or high survival features described herein can be determined in an image obtained from a tissue of the subject. The image can be, for example, a whole slide image (WSI), or a portion thereof, e.g., a tile derived from a WSI. In exemplary embodiments, the tissue is derived from a biopsy obtained from the subject, e.g., a mesothelioma biopsy. Suitable sources of tissue for a mesothelioma biopsy are known in the art, and include without limitation, tissue samples obtained from a needle biopsy, an endoscopic biopsy, or a surgical biopsy. In exemplary embodiments, the image is derived from a thoracentesis biopsy, a thoracoscopy biopsy, a thoracotomy biopsy, a paracentesis biopsy, a laproscopy biopsy, or a laparotomy biopsy.

Tissue sections can be processed for image analysis using any suitable methods and stains for histopathology analysis. For example, the tissue sections can be stained with hematoxylin and eosin, alkaline phosphatase, methylene blue, Hoechst stain, and/or 4', 6-diamidino-2-phenylindole (DAPI).

In one aspect, the invention provides a method for determining the prognosis of a subject known or suspected to have mesothelioma, using the low survival features and/or high survival features described herein. In an exemplary embodiment, the method comprises accessing an image or plurality of images, e.g., a biopsy image or plurality of biopsy images, obtained from the subject, identifying a region of interest in the image(s), and determining the presence or absence of a set of discriminative features in the image(s) that are indicative of mesothelioma prognosis. The discriminative features in the image can include any combination of the low survival features and/or high survival features described herein. For example, the method can comprise determining the presence or absence of one, two, three, four, five, six, seven, eight, nine, ten, eleven, twelve, or more low survival features, optionally in combination with determining the presence or absence of one, two, three, four, five, six, seven, eight, nine, ten, eleven, twelve, or more high survival features. In other embodiments, the method can comprise determining the presence or absence of one, two, three, four, five, six, seven, eight, nine, ten, eleven, twelve, or more high survival features, optionally in combination with determining the presence or absence of one, two, three, four, five, six, seven, eight, nine, ten, eleven, twelve, or more low survival features. In some embodiments, the method comprises defining a set of features selected from tumor grade, pleomorphism, atypia, cellular shape, cellular morphology, vascularization, inflammation, stromal morphology, vacuolization, fibrosis, sarcomatoid components, and combinations thereof, in the image or plurality of images.

In some embodiments, the region of interest is a tumor region. In other embodiments, the region of interest is a stromal region. For example, the region of interest can include a stromal region near or adjacent to a tumor region. In other embodiments, the region of interest can include tumor and stromal components.

The methods described herein can further comprise determining the set of discriminative features using a computer program comprising code instructions for extracting a plurality of feature vectors from the image, as provided above.

A prognosis of the subject can be made based on the presence or absence of low survival features and/or high survival features, and combinations thereof, in the image or plurality of images. In one embodiment, the prognosis is made by a pathologist upon manual examination of the image or plurality of images. In other embodiments, the prognosis is made using a computer program comprising code instructions for executing a classification algorithm, as described above. The classification algorithm can determine a classification for the subject based on a plurality of feature vectors extracted from the biopsy image. In embodiments, the classification algorithm is trained using at least a set of training images comprising biopsy images obtained from a plurality of mesothelioma subjects of known survival duration.

The classification algorithm can compute a score for the subject, which is indicative of the estimated duration of survival of the subject. Notably, the methods described herein allow a continuous risk score to be determined for a subject known or suspected of having mesothelioma, in place of or in addition to classification of the subject into discrete categories, e.g., EMM, SMM, etc. The continuous risk score of a test subject can be plotted against the scores obtained from a plurality of mesothelioma subjects of known survival duration, to identify the estimated duration of survival of the test subject.

(C) Generating a Classification Model for Mesothelioma

Figure 8:
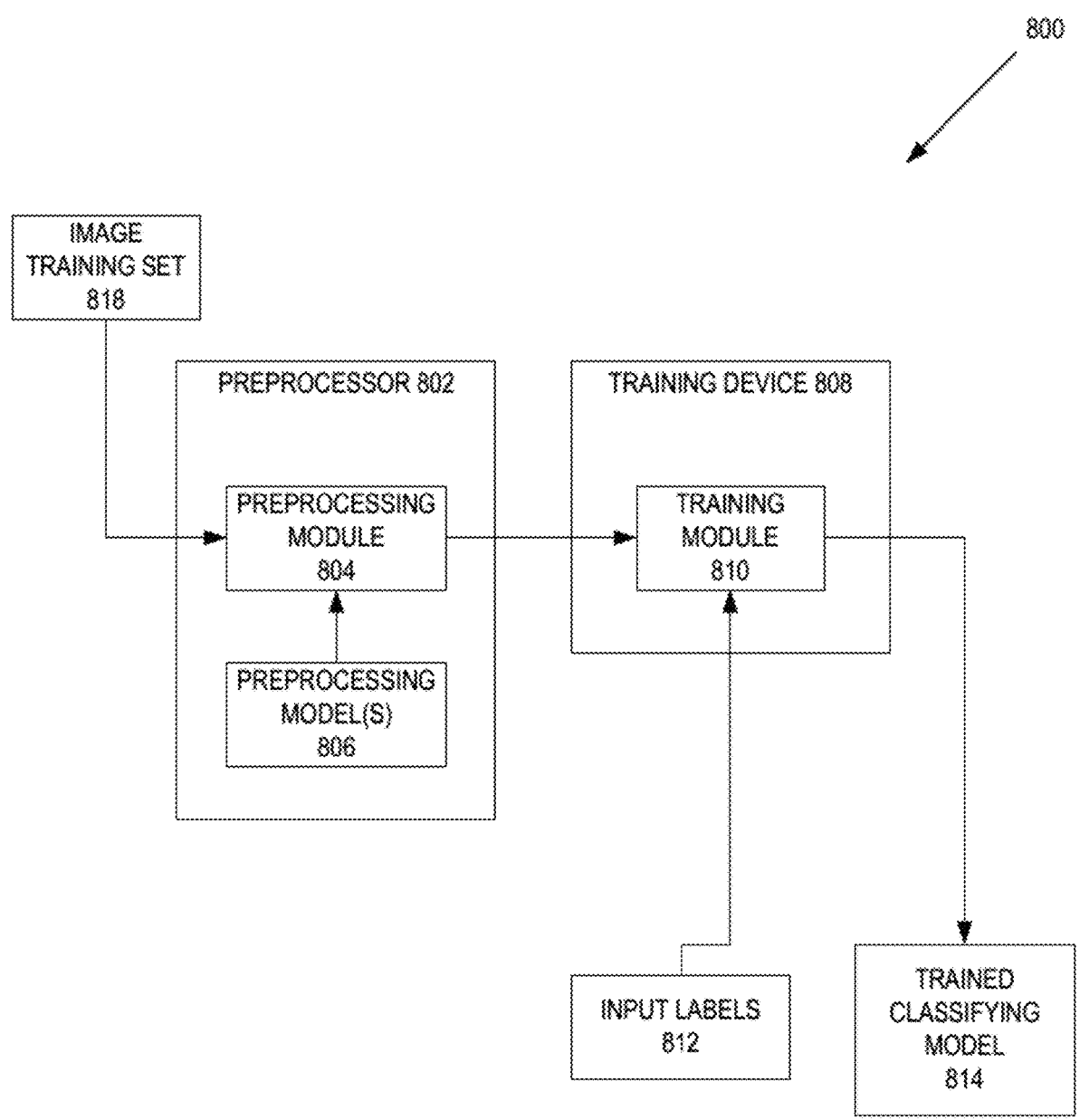
FIG. 8 is a block diagram of one embodiment of a system for training a classification model using a set of training images.

As per above, process 200 uses trained model(s) to determine the subset of tiles and/or label(s) for each input image. In one embodiment, process 200 uses a trained model for the image segmentation, scoring convolutional neural network, and the classification. In a further embodiment, some of the models used in FIG. 2 are trained end-to-end, where the models are trained together. In this embodiment, some of the models used in FIG. 2 can be trained together, such as the MLP used to classify the image and the one dimensional convolutional neural network used to score the tiles. In addition, other models used in FIG. 2 can be trained separately on different training sets (e.g., the ResNet model, U-Net, and/or other types of models). FIG. 8 is a block diagram of one embodiment of a system 800 for training a classification model using a set of training images 816. In FIG. 8, the system 800 includes a preprocessing device 802 that is coupled to a training device 806. In one embodiment, the preprocessing device 802 receives the image training set 816 and generates set of features vectors for each of the images in the images training set 816. The training device 808 can receive the feature vector sets and train a classifying model 814 using input labels 812 associated with the image training set 816. While in one embodiment, the preprocessing device 802 generates the feature vectors and the training device 808 trains the training images, in alternate embodiments, a single device can perform both functions, the devices can performs some or all of the functions of the other device, and/or a combination therein. The training is further described in FIG. 9 below.

Figure 9:
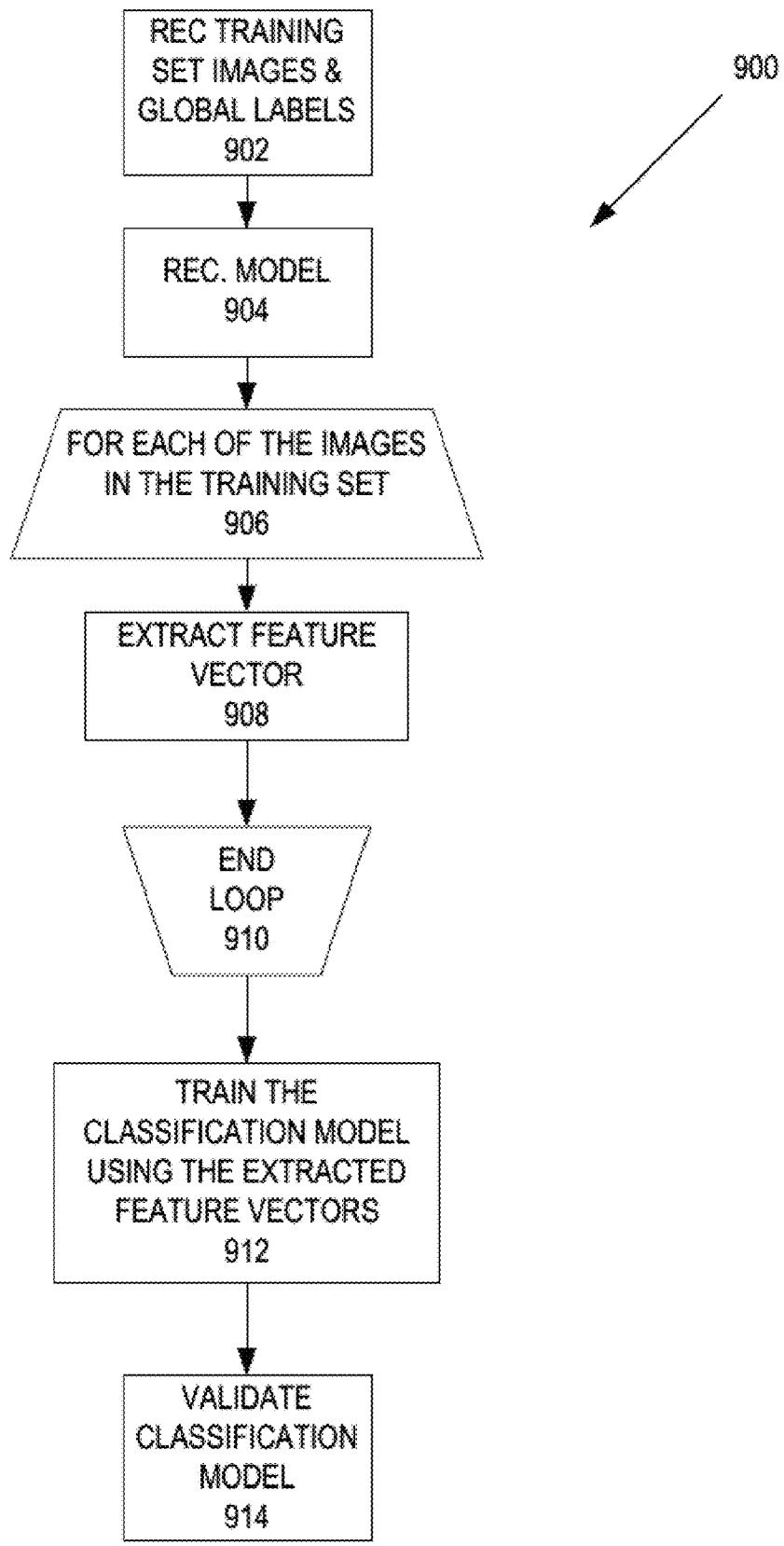
FIG. 9 is a flow diagram of one embodiment of a process to train and validate a classification model.

FIG. 9 is a flow diagram of one embodiment of a process 900 to train and validate a classification model for mesothelioma histopathology images. In one embodiment, the classification model can include one or more separate models used for the classification process described in FIG. 3 (e.g., MLP and/or the one dimensional convolutional neural network). In FIG. 9, process 900 begins by receiving a training set of mesothelioma histopathology images at block 902. At block 904, process 900 receives the model. In one embodiment, the model is a classification model, such as a MLP model and/or other models described elsewhere.

Process 900 performs a processing loop (blocks 906-910) to generate a set of feature vectors for the training set of images. At block 908, process 900 extracts the feature vector for an image in the training set. In one embodiment, process 900 extracts the feature vector as described in FIG. 2 above. For example and in one embodiment, process 900 uses a ResNet-50 convolutional neural network to determine the feature vector for each tile of a tiled segment image as described in FIG. 2 above. In one embodiment, process 900 generates a set of feature vectors for the training image. In addition, process 900 can perform data augmentation during the training of the method to improve the generalization error. This data augmentation can be done by applying various transformations on the tiles such as rotations, translations, cropping, adding noise to the image, modifying the intensity of particular colors, or changing the contrast.

The process loop ends at 910.

Process 900 trains the model(s) using the extracted feature vectors for the training set of images and input labels for the training set of images at block 912. In one embodiment, process 900 trains the one dimensional convolutional neural network producing the scores and the MLP classification model using input labels of the training set of images. In this embodiment, process 900 iteratively trains the model(s) by computing the score sets for the training image, predicting the labels, determining differences between the predicted labels and the input labels, optimizing the model(s) based on the difference (e.g., computing new weights for the model(s)), until the differences are within a threshold. While in one embodiment, process 900 trains the model to predict a single label for the image (e.g., a risk score), in alternate embodiments, process 900 can be trained to predict multiple global labels for the image. In one embodiment, process 900 can be trained to perform a multi-task learning environment to predict multiple global labels. For example and in one embodiment, the classification model (e.g., the MLP and/or other model(s) described elsewhere) can be trained to predict multiple labels at once in the multi-task learning environment (e.g., survival or disease-free survival, and/or other predictions using the resulting feature vector (e.g., clinical data, tumor size, vascular invasion, necrosis, and/or other types of predictions). In order to determine the adequacy of the training, process 900 validates the classification model at block 914. Validation is further described in FIG. 10 below.

Figure 10:
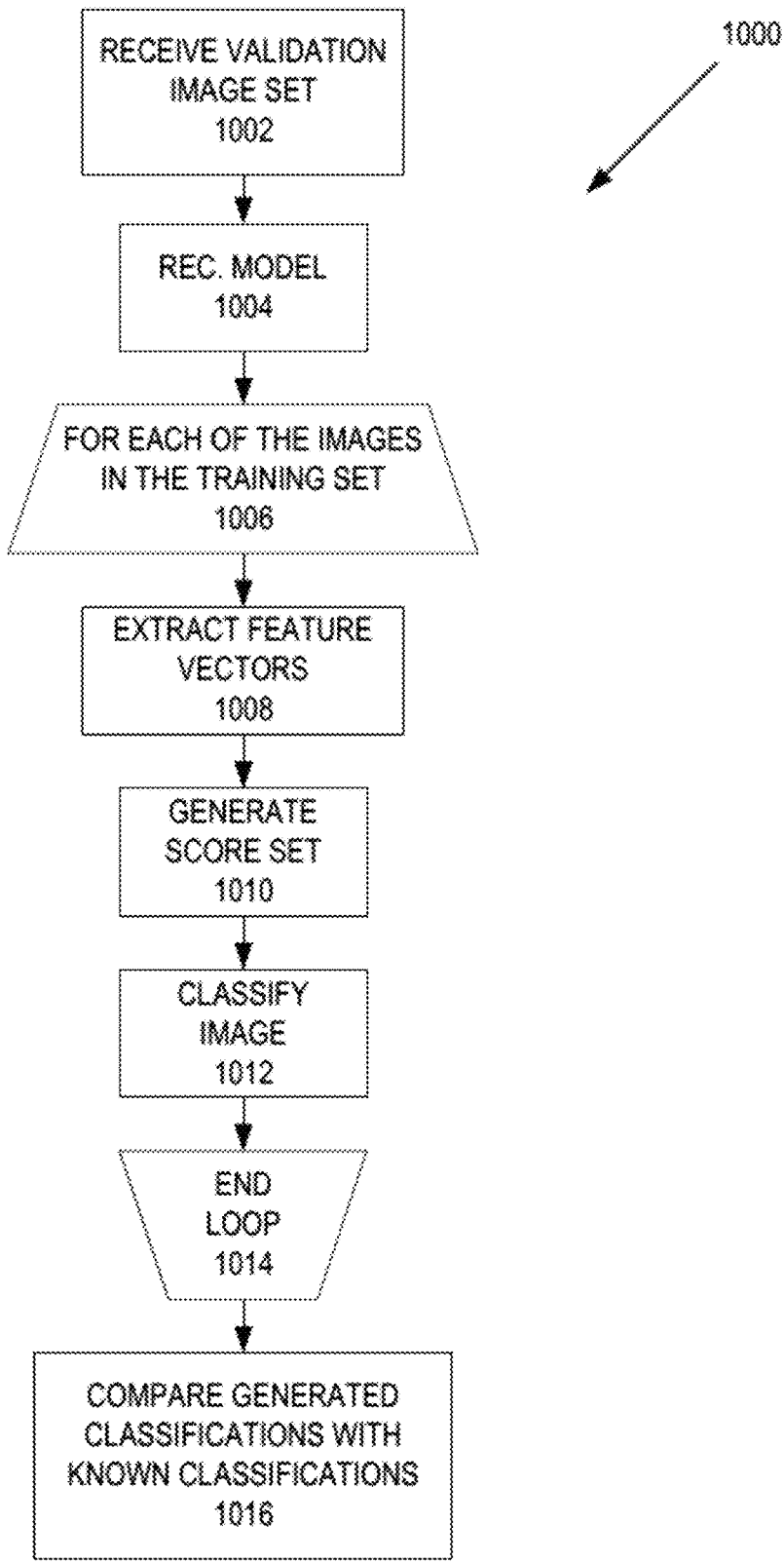
FIG. 10 is a flow diagram of one embodiment of a process to validate a classification model.
Figure 11:
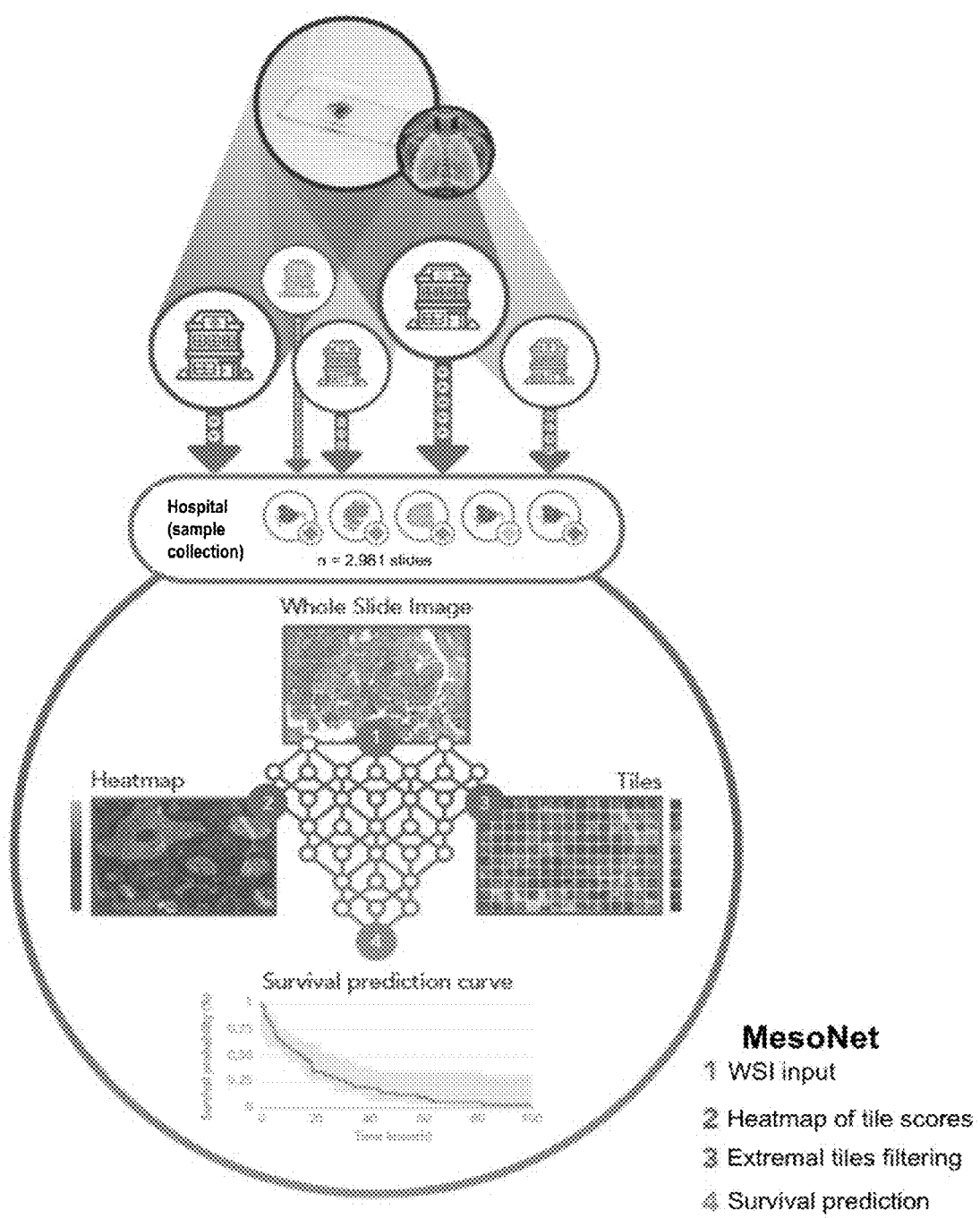
FIG. 11 depicts the layout of MesoNet. Mesothelioma histology slides collected at different French hospitals were centralized by the Centre Léon Bérard in the MESOPATH/MESOBANK database. All the slides were blindly annotated by three expert pathologists in the field. A predictive model was trained for overall survival using whole slide images only, without expert-derived data. The model points to tiles of interest that are positively or negatively associated with survival.
Figure 12:
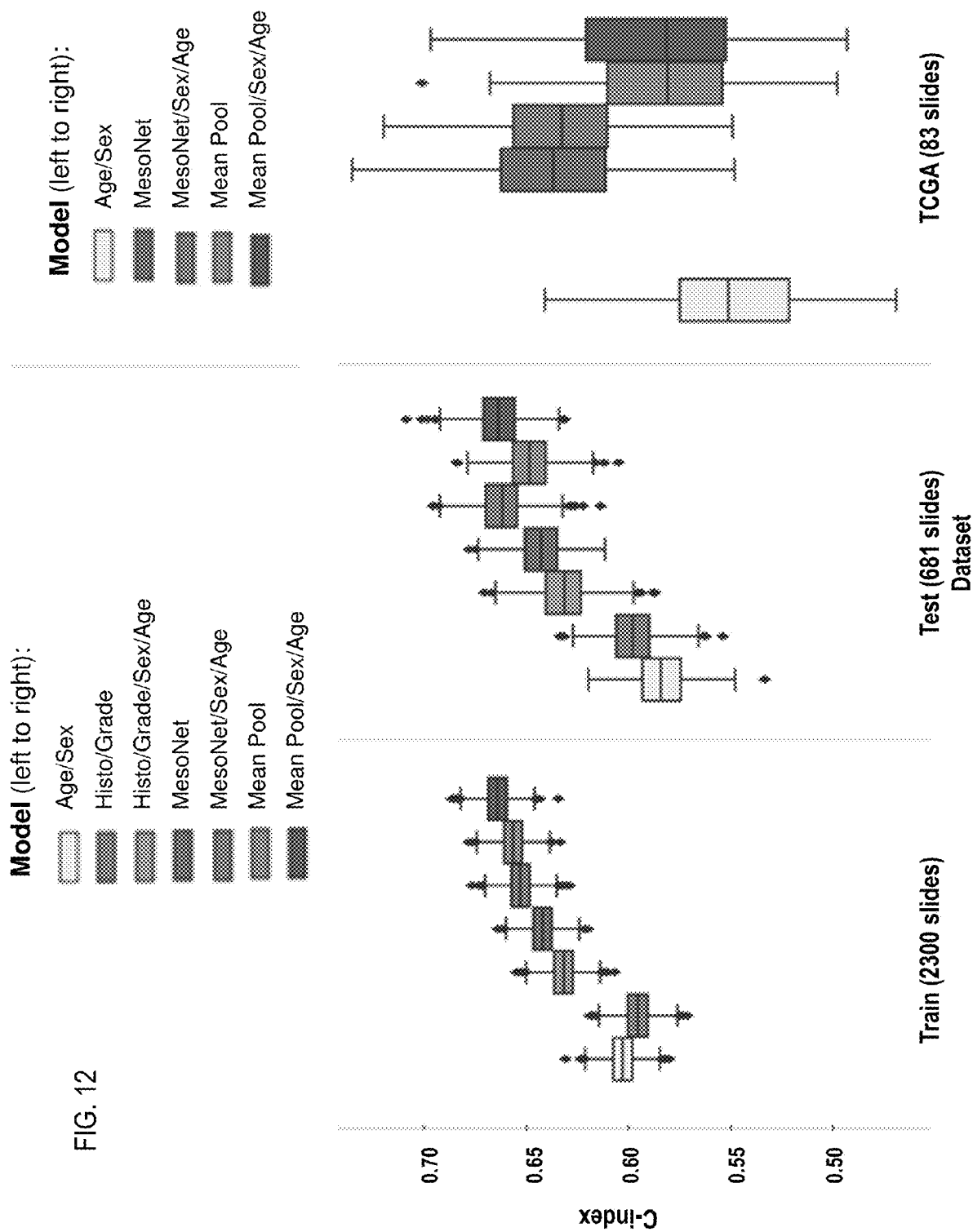
FIG. 12 shows a comparison of performance between MesoNet and models that include additional non-pathology variables such as age and sex to predict Malignant Mesothelioma patient overall survival.

In FIG. 9, process 900 trained a classification model that is used to classify images. How good the classification model can be checked by validating the classification model using the training set of images as inputs and computing one or more labels. FIG. 10 is a flow diagram of one embodiment of a process to validate a classification model. In FIG. 10, process 1000 begins by receiving a validation image set at block 1002. In one embodiment, the validation image set is the same as the training set. In another embodiment, the validation set can be different from the training image set. For example and in embodiment, an image set that has been labeled for a particular type of image (e.g., mesothelioma histopathology images) can have some image selected for use in training the models and other images from this set be used for validating the trained models. At block 1004, process 1000 receives the models used for classifying the validation image sets. In one embodiment, the model is a classification model, such as a MLP model described above.

Process 1000 performs a processing loop (blocks 1006-1014) to generate a set of image labels for the validation image set. At block 1008, process 1000 extracts the feature vectors for an image in the validation image set. In one embodiment, process 1000 extracts the feature vector as described in FIG. 2 above. For example and in one embodiment, process 1000 uses a ResNet-50 convolutional neural network to determine the feature vector for each tile of a tiled segment image as described in FIG. 2 above. In one embodiment, process generates a set of feature vectors for the validation image set. Process 1000 generates a score set for the validation image set using the set of feature vectors at block 1010. In one embodiment, process 1000 generates the score set for the image by using convolutional 1D layer to create a score for each tile as described in FIG. 3 above. In this embodiment, process 1000 selects a subset of tiles for the image, where this subset of tiles is used to generate the tiles scores. Furthermore, process 1000 classifies each of the images using the trained classification model at block 1012.

In one embodiment, process 1000 uses a multi-layer perceptron (MLP) with two fully connected layers of 200 and 100 neurons with sigmoid activation to classify the images in the validation image set. The process loop ends at 1016.

With the classifications for the validation image set, process 1000 can compare the generated classifications with the known classifications of images in the validation image set. In one embodiment, any type of metric that compares differences or distances between labels can be used. For example and in one embodiment, process 1000 can use the area under the receiver operating characteristic curve (ROC-AUC) to determine a comparison between the generated classifications and the known classifications of images in the validation image set when the prediction task is a binary task. In another embodiment, process 700 can use the area under the precision recall curve (PR-AUC) to determine a comparison between the generated classifications and the known classifications of images in the validation image set when the binary labels are unbalanced. In another embodiment, when predicting survival, process 700 can use the concordance index (c-index) to determine a comparison between the predicted risk ordering of the data points and the known ordering.

The processes and displays presented herein are not inherently related to any particular computer or other apparatus. Various general-purpose systems may be used with programs in accordance with the teachings herein, or it may prove convenient to construct a more specialized apparatus to perform the operations described. The required structure for a variety of these systems will be evident from the description below. In addition, the present invention is not described with reference to any particular programming language. It will be appreciated that a variety of programming languages may be used to implement the teachings of the invention as described herein.

EXAMPLES

The advent of deep learning and the availability of thousands of scanned histology slides provides a new opportunity to revisit the problem of diagnosing and predicting cancer, and predicting natural disease evolution in cancer. However, this approach is usually seen as black-box, that is, it is difficult to understand what image features contribute to the prediction. To address these issues, a new prediction model, described herein as "MesoNet," was developed. MesoNet employs a deep-learning algorithm specifically customized to analyze large images, such as whole slide images (WSIs), without any local annotation of the slide by a pathologist. MesoNet was trained on 2,981 MM patients. MesoNet can refine the prognosis of mesothelioma using only routinely generated data, while providing an interpretable-by-design supervised learning model to predict patient survival from tumor histology. In addition, MesoNet has identified new histological biomarkers that can be used for mesothelioma prognosis.

Example 1—Building and Training a Prediction Model (MesoNet)

I. Building MesoNet

A recently described algorithm (Courtiol et al., Classification and Disease Localization in Histopathology Using Only Global Labels: A Weakly-Supervised Approach. (2018) Preprint at https://arxiv.org/abs/1802.02212) specifically designed to address the scenario of non-annotated pathology slides was adapted to build MesoNet. The adapted algorithm can train deep-learning systems from whole-slide multi-resolution gigapixel (100,000 pixels by 100,000 pixels) images with only global data labels to create prediction models. Various steps involved in building the model are summarized in FIG. 4. First, whole slide images of MM were preprocessed and divided into small 112×112 μm squares (224 pixels×224 pixels), called "tiles". Then, these tiles were fed into the network architecture, which assigned a "survival score" to each tile, through an iterative learning process. Finally, the network selected the tiles of each whole slide image that were the most relevant to predict the patient's overall survival. These steps are further described later.

II. The MESOPATH/MESOBANK Dataset

The MESOPATH/MESOBANK database is an exhaustive repository of national data and samples pertaining to mesothelioma. In France, a pathologist or clinician has to send a mandatory declaration to the French National Institute of Health for all suspected cases of mesothelioma. Each case is then registered in the database and histologically certified through a standardized procedure of certification and blindly evaluated by three pathologist experts in the field, systematically reviewing hematoxylin, eosin, and saffron (HES) slides for morphology and immunohistochemistry using a panel of 10 antibodies, with at least two positive and two negative markers for mesothelial cells. All glass slides for evaluation were systematically scanned and archived at the Léon Bérard Cancer Center with their epidemiological and clinicobiological annotations.

III. Demographic and Clinical Characteristics of the MESOPATH/MESOBANK Database

This cohort consisted of 2,981 patients for which digitized whole slide images of HES-stained mesothelioma histology slides, as well as additional clinical information, were available (Table 1). A subset of the samples has been collected through needle biopsies (n=38).

TABLE 1

Demographic and clinical characteristics of the MESOPATH/MESOBANK dataset

| Characteristics | Summary |
| --- | --- |
| Patients | 2,981 |
| Age (years) | |
| Range | 21-97 |
| Median | 74 |
| Gender | |
| Female | 814 (27.3%) |
| Male | 2,167 (72.7%) |
| Follow-up (months) | |
| Range | 0-292 |
| Median | 19.4 |
| Deaths | 2,378 (79.8%) |
| Grade | 1760 (59.0%) |
| G1 | 390 (22.2%) |
| G2 | 913 (51.8%) |
| G3 | 457 (26.0%) |
| Histological subtype | |
| Epithelioid | 2,404 (80.6%) |
| Biphasic | 336 (11.3%) |
| Sarcomatoid | 241 (8.1%) |

IV. Histological Subtyping

Every image contains a histology slide of the mesothelioma and pleura, at a magnification of 20× (resolution 0.5 μm per pixel). Each slide is stained with HES, a classical trichromatic coloration that enhances the collagen composition of each tissue. Finally, the pathology diagnosis is made following the WHO recommendation as cited in Galateau-Salle, et. al., hereby incorporated by reference. (Galateau-Salle, F., Churg, A., Roggli, V. & Travis, W. D. The 2015 world health organization classification of tumors of the pleura: Advances since the 2004 Classification. *J. Thorac. Oncol.* 11, 142-154, 2016), with classification into one of three subtypes (epithelioid, sarcomatoid, or biphasic) if the sample contains at least 10% of both epithelioid and sarcomatoid components, which can be influenced by the size of the sample.

V. Training and Testing MesoNet

To train and test MesoNet, a new dataset (MESOPATH/MESOBANK) consisting of 2,981 patients from multiple institutions was assembled. (Galateau-sallé, F. et al. [The French mesothelioma network from 1998 to 2013]. *Ann. Pathol. Elsevier Masson* 34, 51-63, 2014, hereby incorporated by reference). The MESOPATH/MESOBANK dataset was partitioned into a training dataset of 2,300 patients which was used to train the model, and a test dataset of 681 patients which was kept entirely separated to assess the performance of each model in an unbiased manner.

A five-fold cross-validation strategy was first used on the training set of 2,300 patients (FIG. 4):

A). Matter extraction: The part of the image that indeed contained matter was first detected. This segmentation was performed using a U-net neural-network approach as described by Ronneberger, et. al., hereby incorporated by reference in its entirety. (Ronneberger, O., Fischer, P. & Brox, T. U-net: Convolutional networks for biomedical image segmentation. *Medical Image Computing and Computer-Assisted Intervention—MICCAI* 2015: 18*th International Conference Munich, Proceedings, Part III*, 2015). All pixels were separated between two classes: pixels of the foreground (containing the matter) and background.

B). Tiling: The parts of the images containing matter were divided into smaller images, called "tiles", of fixed size (for example, 224×224 pixels). The number of tiles depends on the size of the matter detected and can vary from a few hundred to 50,000. The extraction was limited to 10,000 tiles, taking into consideration the computation time and required memory.

C). Feature Extraction: Feature extraction was performed using ResNet50. (He, K., Zhang, X., Ren, S. & Sun, J. Deep Residual Learning for Image Recognition. in 2016 *IEEE Conference on Computer Vision and Pattern Recognition (CVPR)*, 2016, doi:10.1109/CVPR.2016.90, hereby incorporated by reference). Already pre-trained for any image recognition task, this network allowed for collection of 2,048 relevant features from each tile. Therefore, a matrix of 10,000 (tiles)×2,048 (features) was obtained for each slide. If there was not sufficient matter in the slide to extract 10,000 tiles, a zero-padding was performed to fill the matrix. At the end of this step, a tensor of dimensions 2,981×10,000×2,048 was obtained.

D). Top and Negative Instances: A convolutional 1D layer was used to create a score for each tile. This convolutional layer performs a weighted sum between all 2,048 features of the tile to obtain this score (weights of this sum are learned by the model). As this convolutional 1D layer is unbiased, all the zero-padding tiles have a score of 0, and thus a reference for a totally uninformative tile. The highest and lowest R scores were selected and used as input for the last step. This architecture determines which tiles are used to make the predictions, and how the algorithm predicts the result.

E). Multi-layer Perceptron (MLP) Classifier: The last step includes a multi-layer perceptron (MLP) with two fully connected layers of 200 and 100 neurons with sigmoid activation. This is the core of the predictive algorithm that transforms the scores from the tiles to a prediction.

The MesoNet model was trained iteratively on ⅘ths of the 2,300 training slides and evaluated on the remaining ⅕th. The model was then evaluated on a test set of 681 patients from MESOPATH/MESOBANK, kept entirely separated from the training set, and a completely independent TCGA dataset of 83 mesothelioma H&E WSIs. (FIG. 9). This allowed testing the robustness of MesoNet to different data preparation protocols, as TCGA slides were collected at different centers and used a different coloration technique (hematoxylin & eosin for TCGA versus hematoxylin & eosin & saffron for MESOPATH/MESOBANK).

VI. Model Improvements

Several improvements were made to the structure of a previous model for analysis of histopathology slides, described by Courtiol et al., (2018) (Preprint at https://arxiv.org/abs/1802.02212).

U-Net segmentation: Initially, segmentation was made using the Otsu algorithm, which is a generally used segmentation method that requires no training. However, this type of segmentation was not sufficiently robust and failed on slides containing artifacts, such as ink marks, for which it returned an empty mast (data not shown). The U-Net method was used instead. It was trained on a few hundred thumbnails of histology images in which matter was manually selected.

Survival loss: A weakly supervised approach was previously applied to classification problems, as described by Courtiol et al., (2018) (Preprint at https://arxiv.org/abs/1802.02212). In the MesoNet model described herein, the last layer of the architecture was changed from "softmax" activation to linear activation, which better fits the prediction of survival and is similar to a regression problem. However, this problem is not equivalent to a regression, because of censored data, and requires a specific loss function, such as the Cox loss function, which allows the use of information from censored data.

Auto-encoding: MesoNet can be subject to over fitting, like many models in machine learning. This recurrent problem in machine learning was solved by reducing the dimension of the input of the prediction part of the network to 512 features instead of 2,048. An autoencoder was used, which consists of a single hidden-layer architecture (of 512 neurons). This prevents MesoNet from over-fitting by finding several singular features in the training dataset and also reduces computation time and required memory.

MesoNet was trained on 200 tiles randomly selected from each slide (a total of 411,400 tiles). The model converged after three epochs to a mean squared error (MSE) of 0.0235.

VII. Assessment of Performance

The Concordance Index (c-index) was used to quantify the concordance between the predicted and true survival time of a set of patients:

$$c\text{-index} = \text{number of concordant pairs} \div \text{number of admissible pairs}$$

The concordant pairs are the pairs of patients that are correctly classified, and the admissible pairs are the pairs of patients that can be ordered. For example, $(i,j)$ is admissible if patients $i$ and $j$ are not censored, or if patient $i$ dies at $t=k$ and patient $j$ is censored at $t>k$. On the contrary, if patient I died at $t=k'$ and patient $j$ is censored at $t<k'$, then $(i,j)$ is not admissible.

Example 2—Comparison of MesoNet to Models Based on Histology Subtype

A comparison was done between MesoNet and the models "Histo", a baseline model using pathologist-provided histology subtype only, "Histo/Grade", using a combination of histological subtype and tumor grade, and "Meanpool", a naïve approach that trains a linear regression from the mean-aggregation of the features of all tiles of each slide. Briefly, for each patient in the MESOPATH/MESOBANK dataset, the subtype of mesothelioma (EMM, BMM, SMM), and the grade of the tumor (I, II, or III) are known. The model "Histo" uses only the subtype of mesothelioma to predict survival. The model "Histo/Grade" uses both the subtype of mesothelioma and the grade of the tumor to predict survival. Both "Histo" and "Histo/Grade" are simple linear regression models (Cox model). The c-index was used to compare the predictive performance of each model. The grading of the TCGA dataset was not consistent with that of the MESOPATH/MESOBANK dataset, and was therefore, not considered in this comparison.

MesoNet significantly outperformed the baseline models on the cross-validation set from the training dataset (cMesoNet(Train)=0.642 vs cHisto(Train)=0.596, $p<0.001$, t-test), the test dataset (cMesoNet(Test)=0.643 vs cHisto(Test)=0.598, $p<0.001$, t-test) and the TCGA dataset (cMesoNet(TCGA)=0.638 vs cHisto(TCGA)=0.584, $p<0.001$; t-test), demonstrating the effectiveness of the algorithm in predicting patient outcome. FIG. 10 shows a comparison between MesoNet and other models including additional non-pathology variables such as age and sex to predict MM patient overall survival. MesoNet performed slightly less well than Meanpool on the MESOPATH/MESOBANK training and test sets (cMesoNet(Train)=0.642 vs cMeanpool(Train)=0.657, $p<0.001$; cMesoNet(Test)=0.643 vs cMesoNet(Test)=0.649, $p<0.001$, t-test) but significantly outperformed Meanpool on the TCGA dataset, for which the performance of Meanpool was much lower (cMesoNet(TCGA)=0.638 vs cMeanpool(TCGA)=0.581, $p<0.001$, t-test), showing that MesoNet is robust when applied to an independent dataset in contrast to aggregated methods, such as Meanpool, in accordance with studies such as Courtiol, et. al (preprint at https://arxiv.org/abs/1802.02212, and hereby incorporated by reference in its entirety). Similar models integrating age and gender were also compared, and MesoNet again outperformed classical models.

Figure 13A:
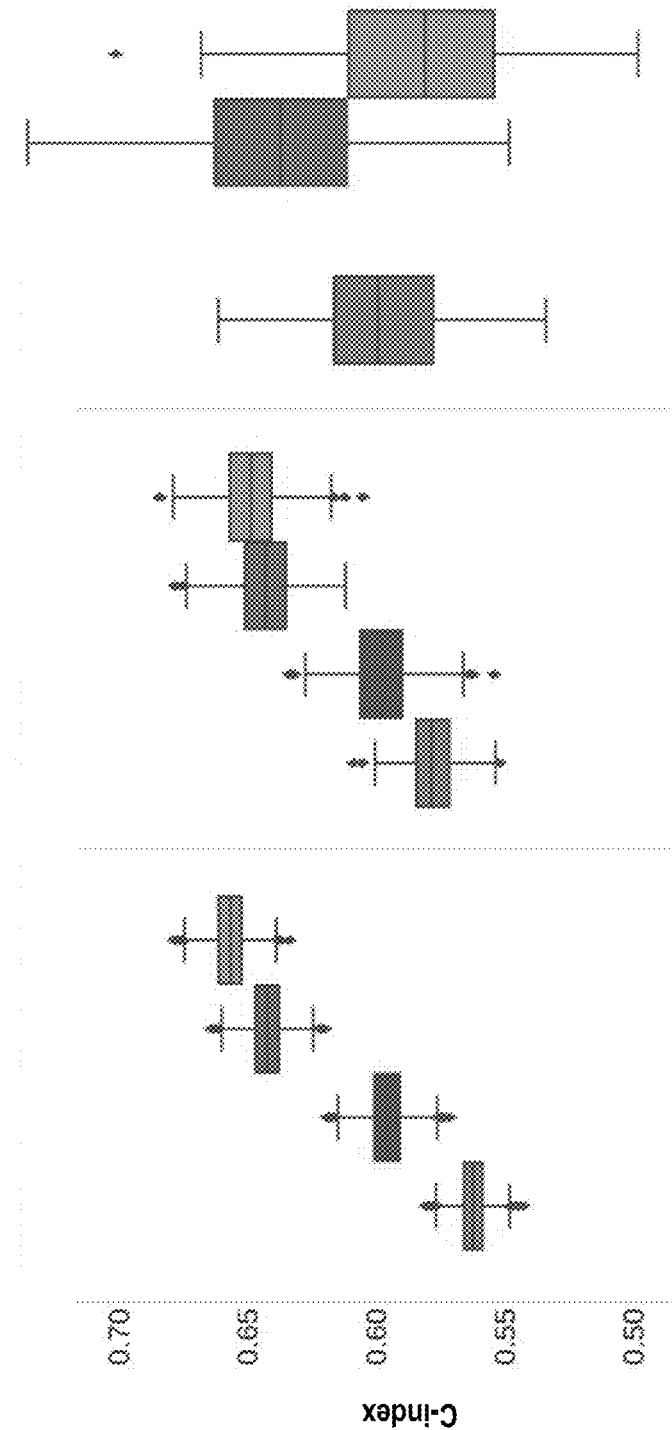
FIGS. 13a-13e compare the performance between MesoNet and other histology-based models to predict MM patient overall survival.
Figure 13B:
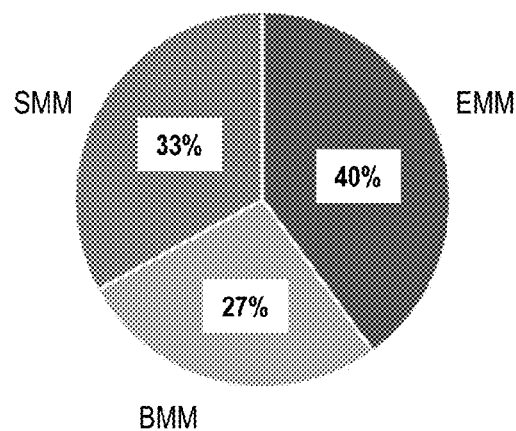
Figure 13B:
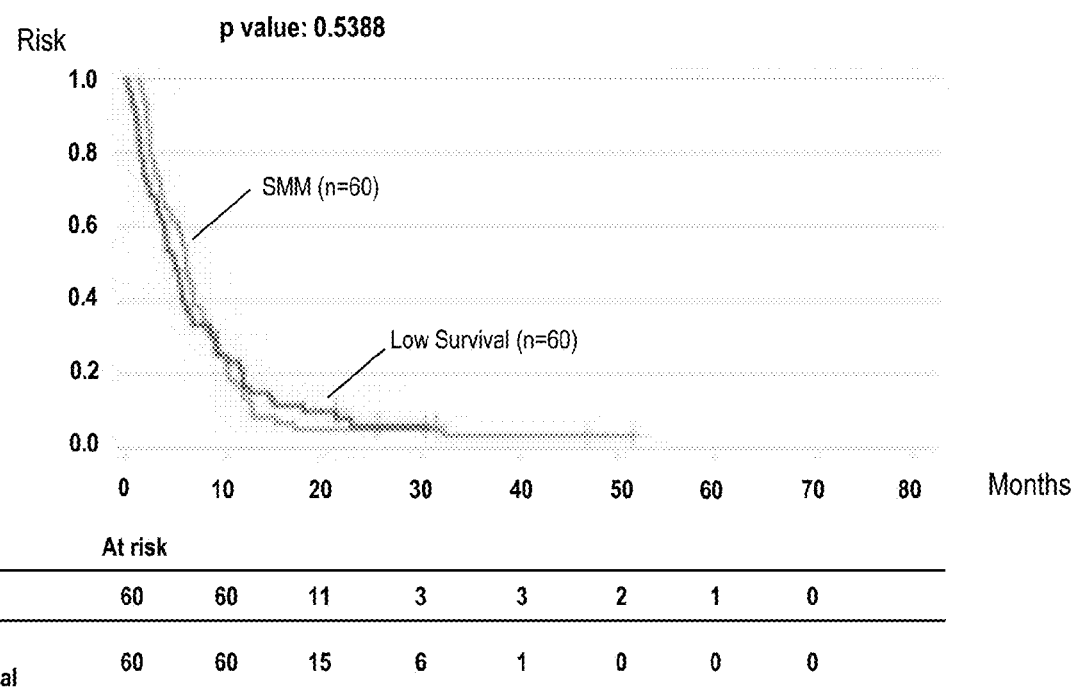
Figure 13C:
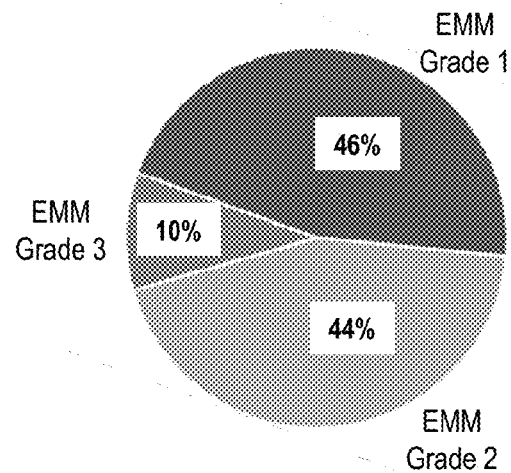
Figure 13C:
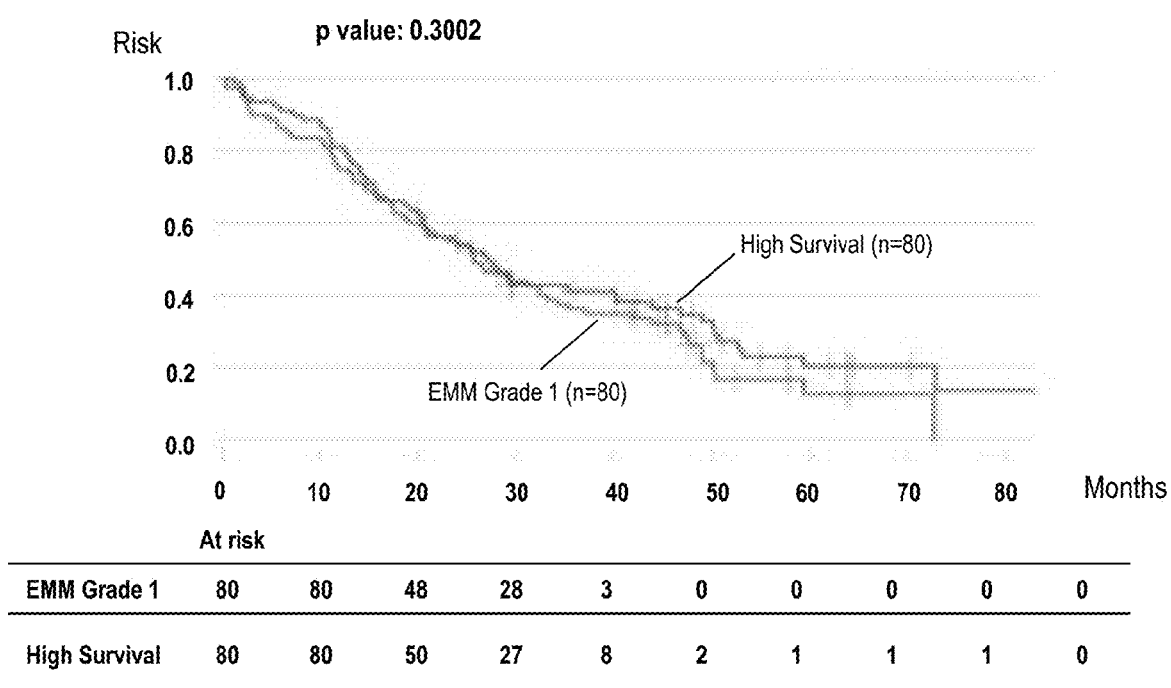
Figure 13D:
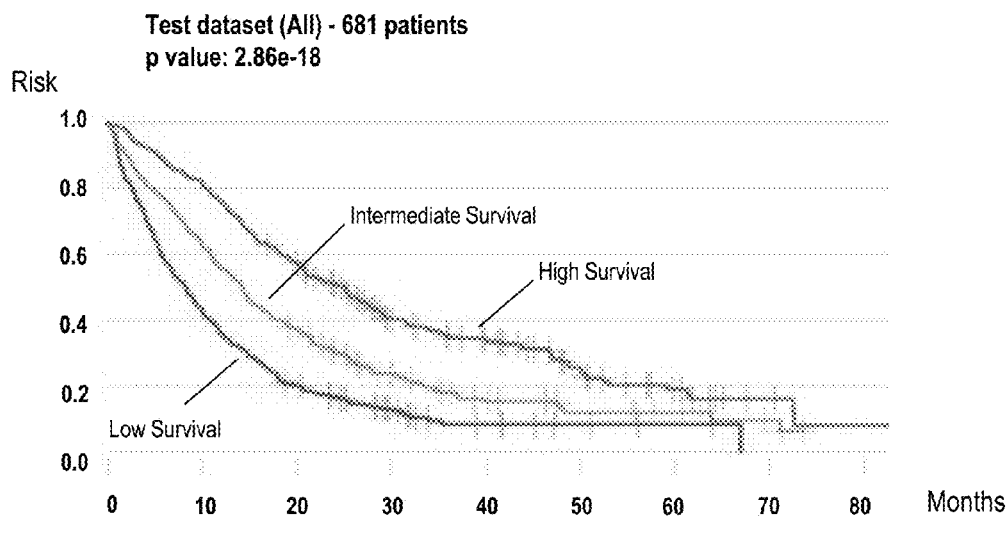
Figure 13D:
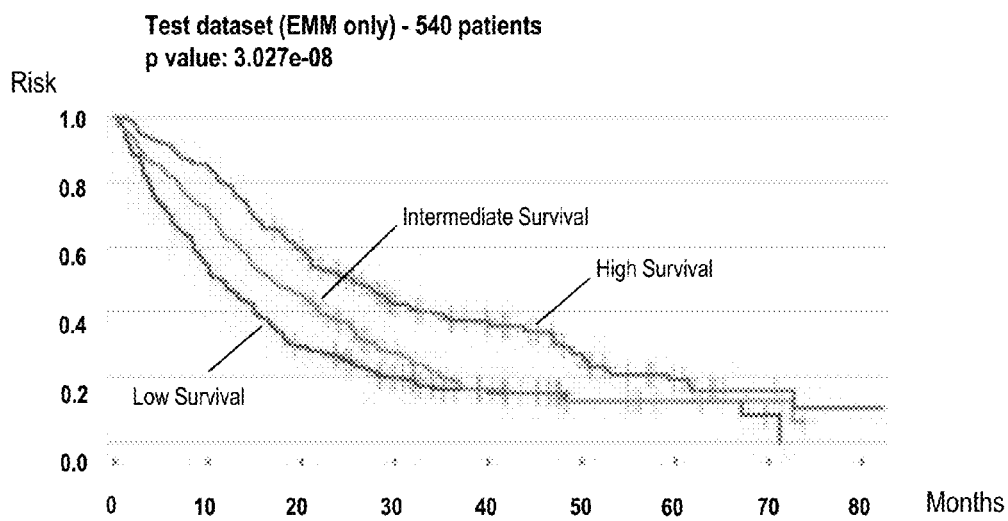
Figure 13E:
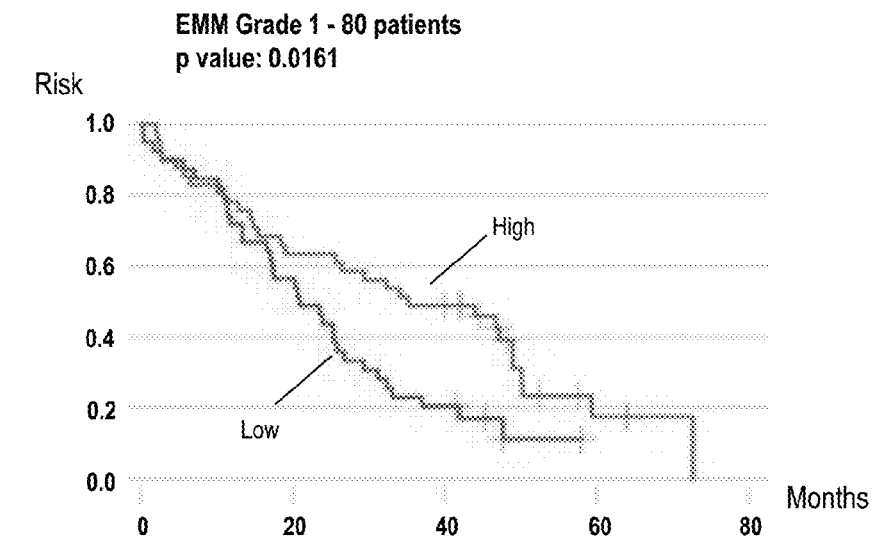
Figure 13E:
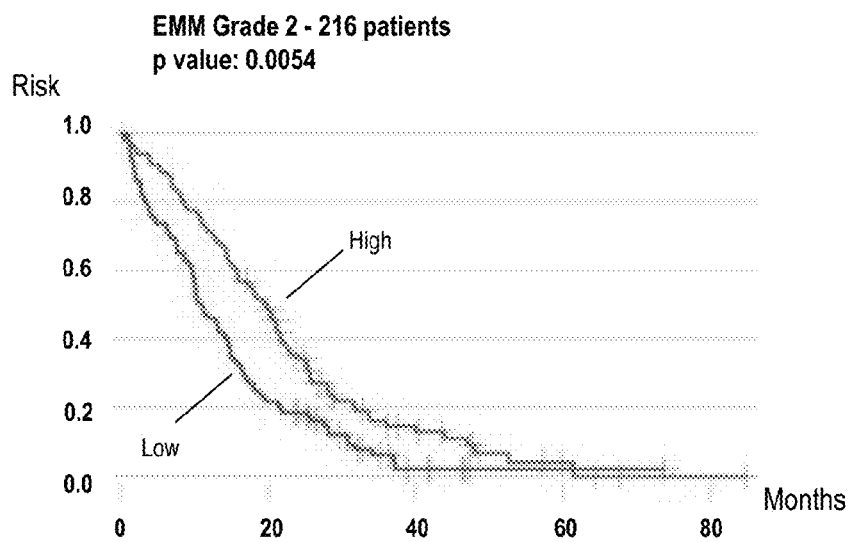
Figure 13E:
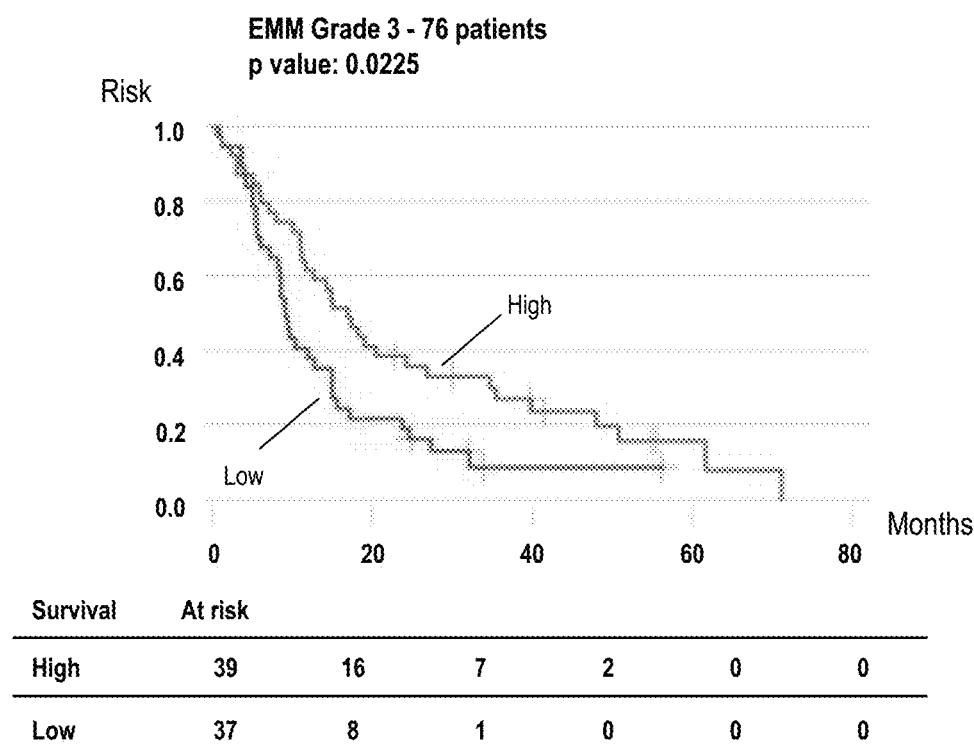

A key advantage of MesoNet over histopathology-based classification is its ability to output a continuous risk score, instead of a discrete patient categorization. Patients were split from the test set into equivalent groups of low, intermediate, and high risk to provide a fair comparison. As expected, these three groups had significantly different outcomes over the entire dataset (FIG. 13d, $p<0.001$, log-rank test). More importantly, similar subgroups were identified with significantly different outcomes amongst the set of EMM patients (FIG. 13d, $p<0.001$, log-rank test) and within each grade (EMM grade 1, $p=0.016$; EMM grade 2, $p=0.005$; and EMM grade 3, $p=0.022$, log-rank test). This shows that MesoNet can provide risk scores independently of histological subtype and grade.

Example 3—Predictive Outcome with Epithelioid Mesothelioma Patients

Grade 1 epithelioid mesothelioma patients are considered to have the best prognosis. This group represented 80 patients in the test dataset, with a median survival of 28.1 months. The 80 patients predicted to have best survival by MesoNet were all epithelioid patients, with a similar prognosis, but with a mix of different grades, showing that MesoNet can also extract predictive features orthogonal to tumor grade (FIG. 13c, p=0.3, log-rank test).

Example 4—Predictive Outcome with Sarcomatoid Patients

When using histology diagnosis made by a pathologist, sarcomatoid patients are associated with a worse prognosis than the other two subtypes. In the test dataset, this subgroup consisted of 60 patients with a median survival of 7.2 months. In comparison, the set of 60 patients predicted to have the worst prognosis by MesoNet consisted of a mix of the three histological subtypes, with only 34% of patients classified as sarcomatoid and 40% of patients classified as epithelioid, supposedly associated with a better prognosis. These two subgroups had comparable outcomes (p=0.53, FIG. 13b, log-rank test), showing that MesoNet can extract predictive features of a poor prognosis that transcend the current histological classification, and can identify a subgroup of epithelioid patients with a very poor prognosis.

Example 5—Comparison of MesoNet Against Aggregated Methods

Figure 14A:
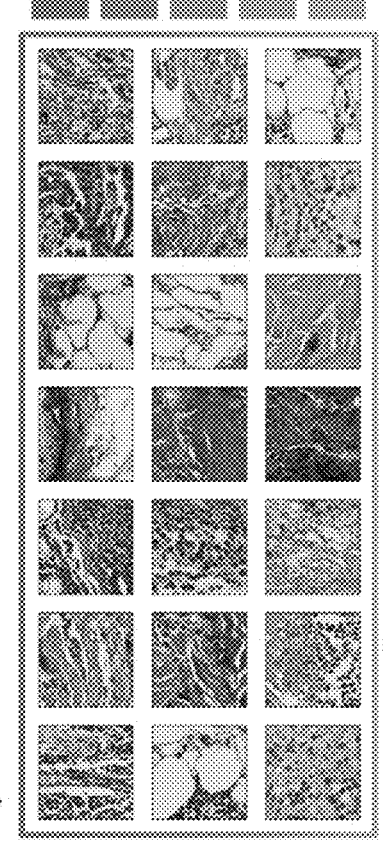
FIGS. 14a-14b show an extraction of extremal tiles associated with prognosis to identify regions of interest.

Another important aspect of MesoNet, with respect to aggregated methods, such as Meanpool, is its interpretability power. The design of the tile scoring system allows scoring of all the tiles for a given patient, which can be represented by a distribution that is shifted towards negative values for patients with a good prognosis and positive values for patients with a poor prognosis (FIG. 14a). This scoring system could be potentially superimposed over a WSI to provide a companion tool for pathologists to identify known or new regions of interest associated with survival for each patient.

Figure 14B:
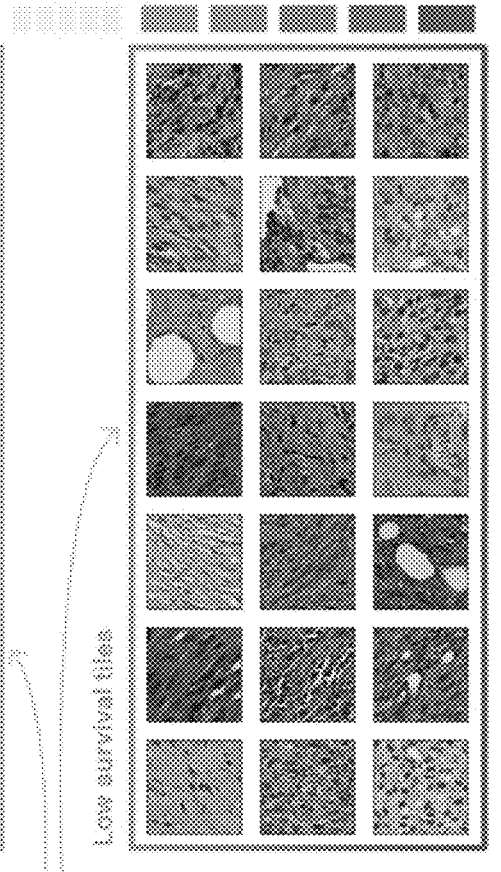
Figure 15A:
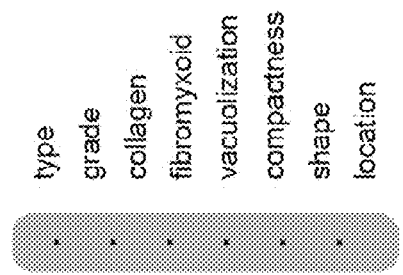
FIGS. 15a-15d is a histological review of tiles of interest.
Figure 15A:
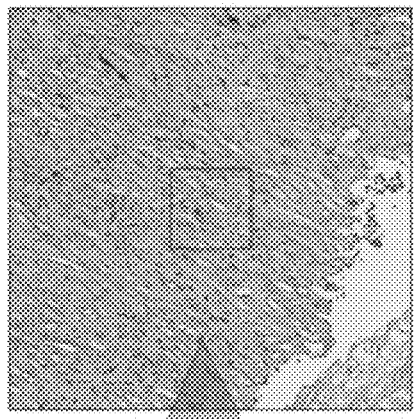
Figure 15A:
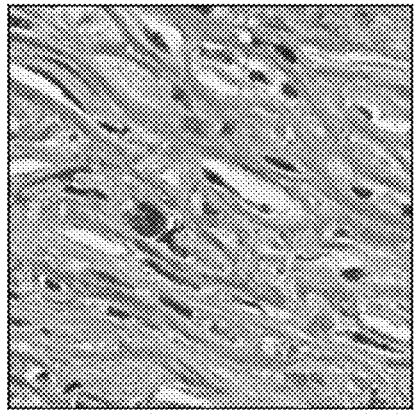
Figure 15B:
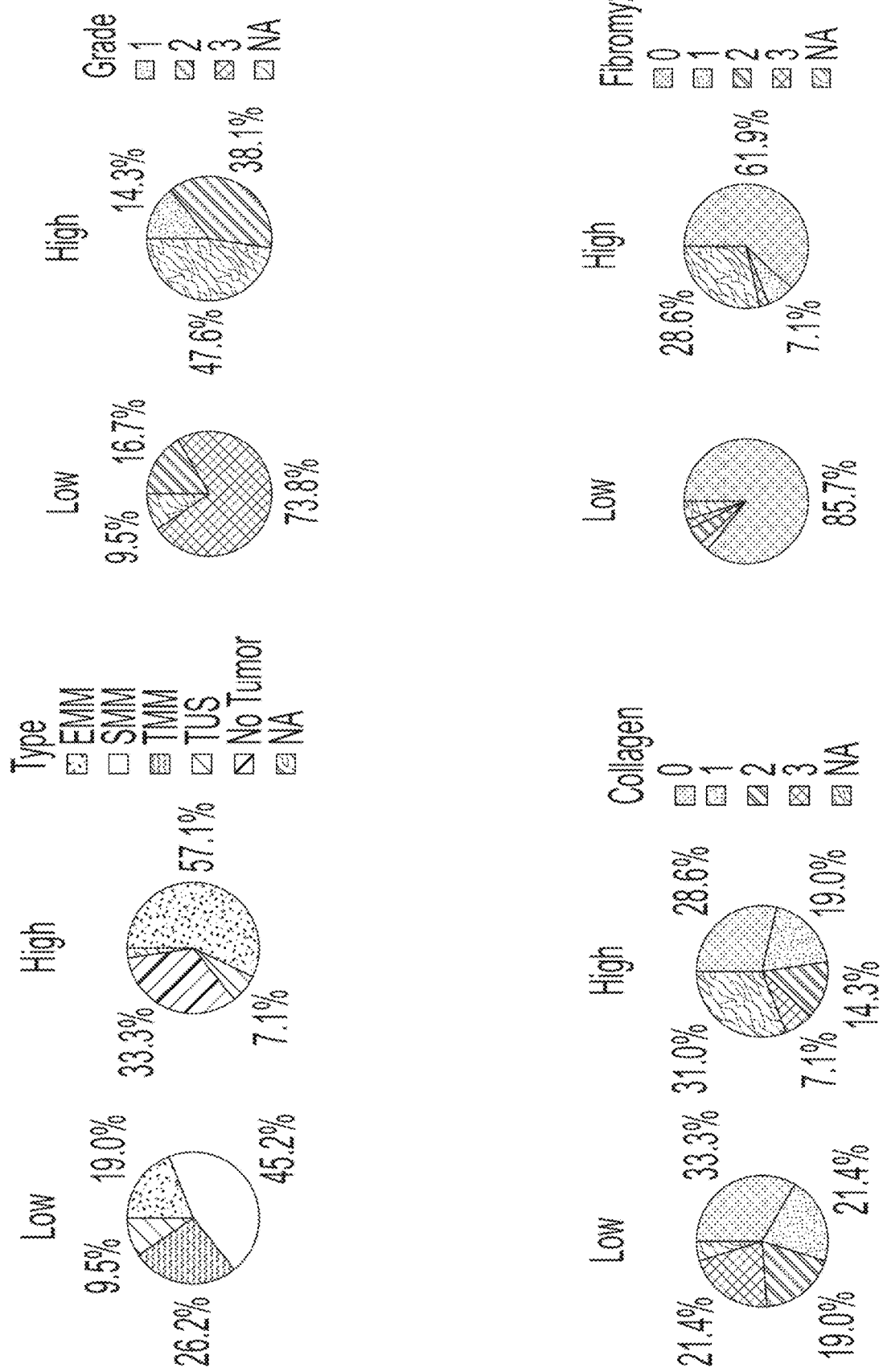
Figure 15B:
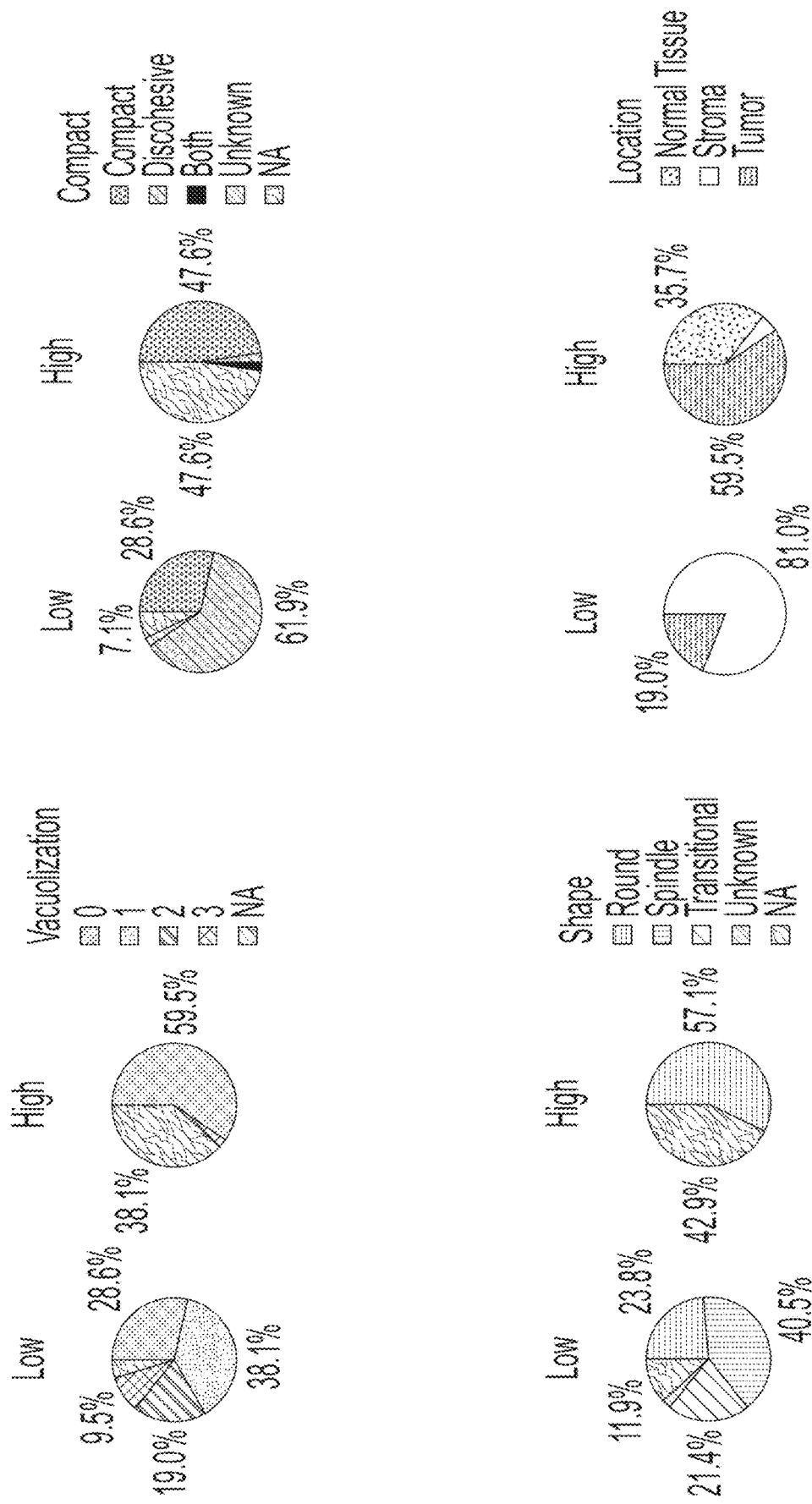
Figure 15C:
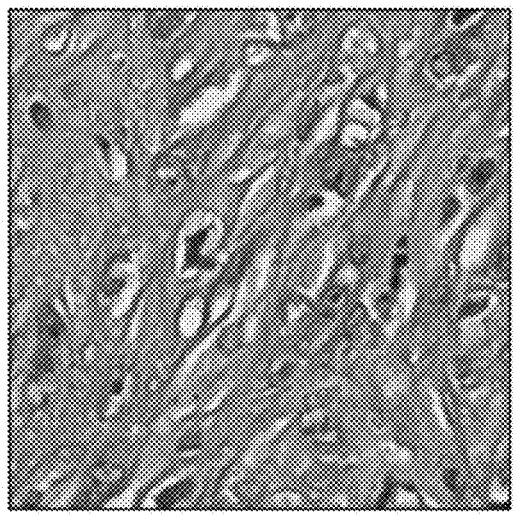
Figure 15C:
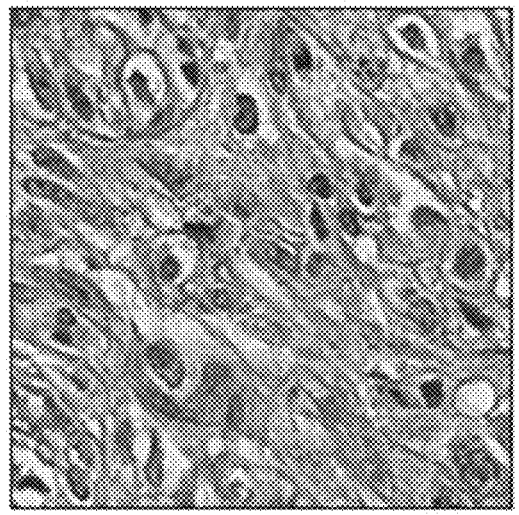
Figure 15C:
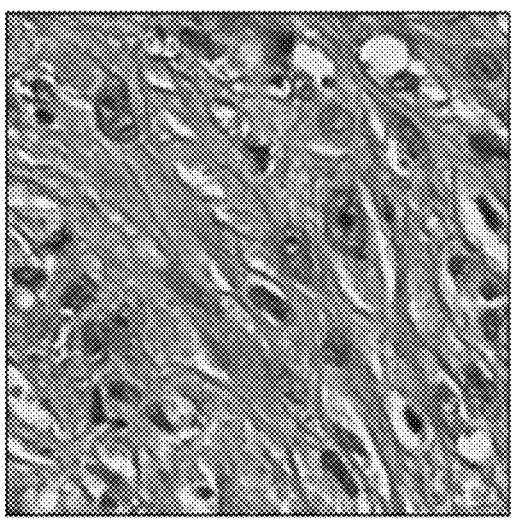
Figure 15C:
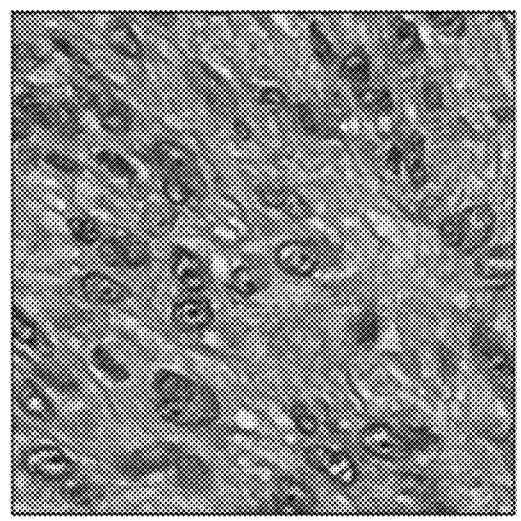
Figure 15D:
Figure 15D:
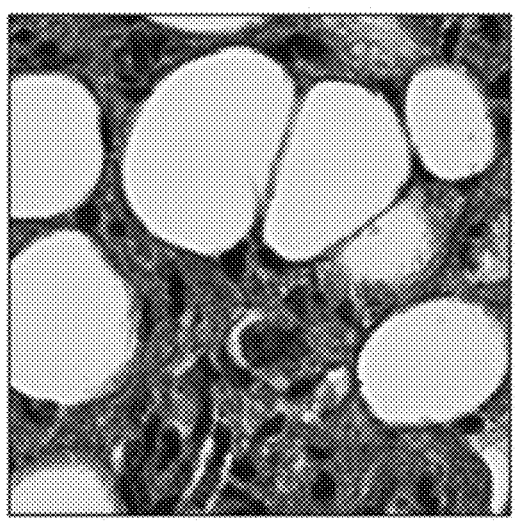

To obtain a disease-centric understanding of histological predictive features, all tile scores were aggregated from the 2,981 patients from the MESOPATH/MESOBANK into a single distribution and extracting the ones associated with high and low survival across patients (FIG. 14b). Two pathologists specialized in mesothelioma histology manually and independently reviewed the extremal tiles extracted by MesoNet (n=42, FIG. 15a). Most tiles associated with low survival were mainly localized in stromal regions, instead of within the tumors (FIG. 15b). Tiles associated with high survival showed a tubular architecture and were well vascularized (FIG. 15b). In contrast, tiles associated with low survival showed a transitional pattern, a provisional histopathological pattern (Galateau-Salle, F. et al., J. Thorac. Oncol. (2018), 13: 1189-1203), higher grade cellular morphology with atypical nuclei, and a characteristic stromal response, consisting of cancer-associated fibroblasts with small vessels unevenly distributed together with inflammatory cells (FIG. 15c). Other tiles associated with low survival were focused on areas of vacuolated and atypical cells in a dense collagenous stromal response, for which the malignancy of the region cannot be confidently assessed by the pathologist during an initial assessment based on H&E staining, without immunohistochemistry. These tiles were named "Tiles of Unknown Significance" (TUS) (FIG. 15d).

Example 7—Analysis of Specific Histological Features (Predictive Vs. Non-Predictive Tiles)

Figure 16:
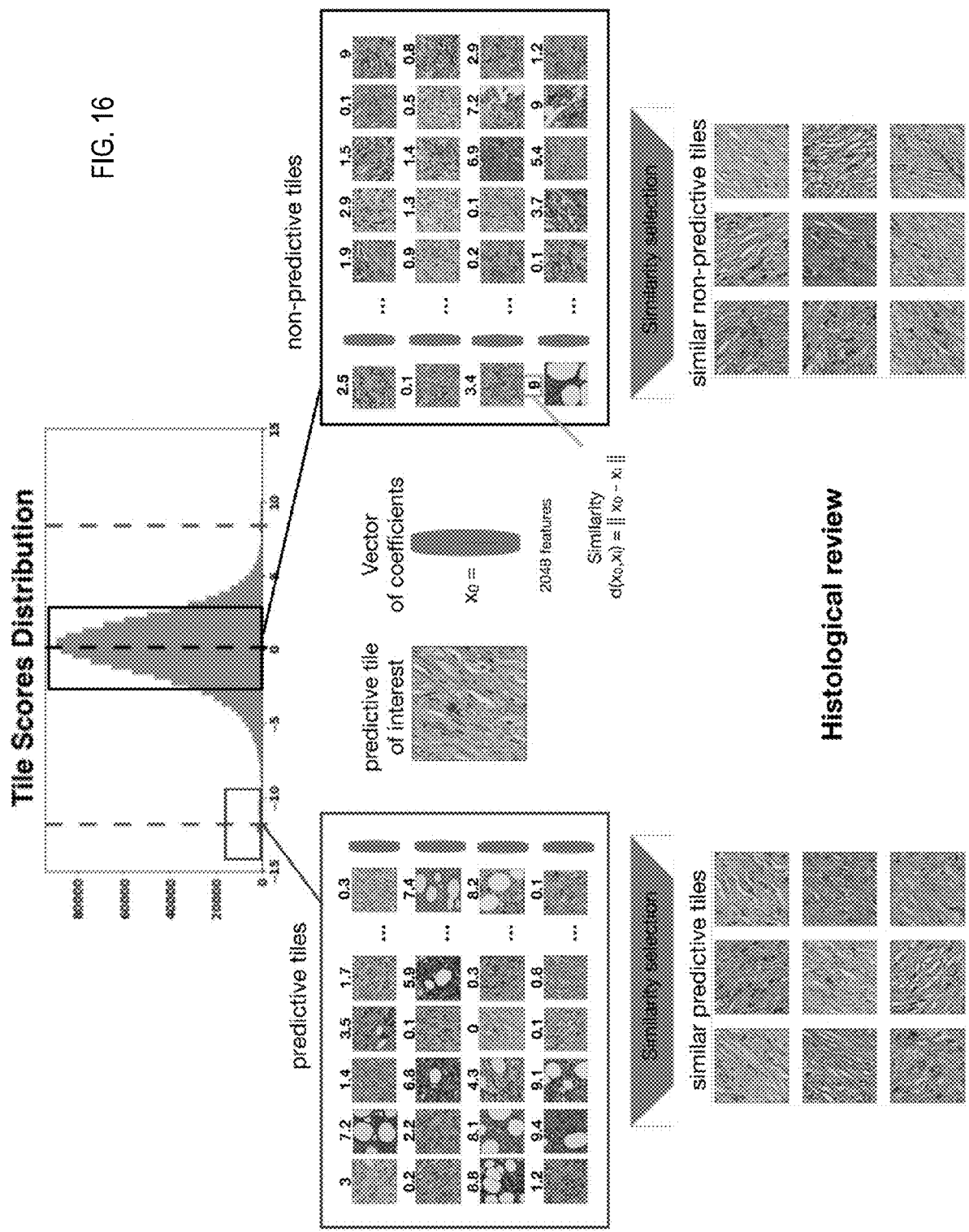
FIG. 16 shows a comparative histological analysis of predictive and non-predictive tiles. The similarity of predictive and non-predictive tiles to a given predictive tile of interest is calculated based on the vector of coefficients obtained with ResNet50. Similar predictive and non-predictive tiles are then reviewed manually for each extremal tile by pathologists.
Figure 17:
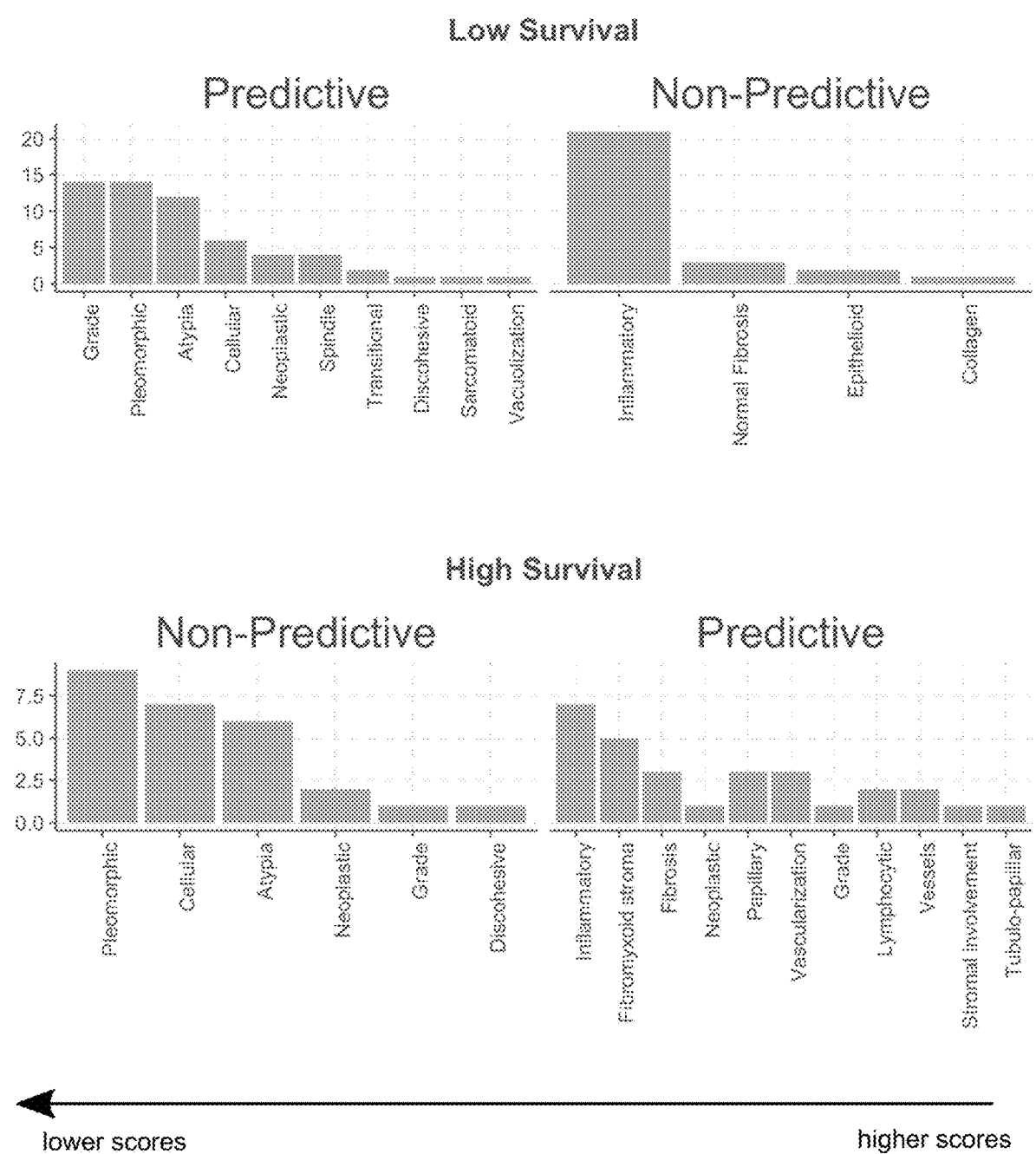
FIG. 17 displays a comparative histological analysis of predictive and non-predictive tiles. A histogram is provided depicting histological features associated with either predictive or non-predictive tiles, that are similar to extremal tiles of high and low survival (n=42). The review was performed independently by two mesothelioma pathologists.

Specific histological features that differentiate predictive and non-predictive tiles for low and high survival were separately analyzed. For the most predictive extremal tiles (n=21 by subgroup), a subsample of nine predictive and non-predictive tiles based on the tile scores that were the most similar according to the vector of coefficient were extracted. (FIG. 16). Two pathologists reviewed and compared the predictive tiles to the non-predictive ones. Predictive tiles associated with low survival were of higher-grade tumors and were more pleomorphic, atypical, and showed a lower inflammatory response (FIG. 17). Conversely, predictive tiles associated with high survival were of lower-grade tumors and were less pleomorphic, atypical, and showed a greater inflammatory response (FIG. 17). Taken together, these results validate that high pleomorphism, atypia and a lower inflammatory response are consistently associated with a lower survival.

Example 8—Analysis of Tiles Associated with Low Survival in EMM Patients

Figure 18B:
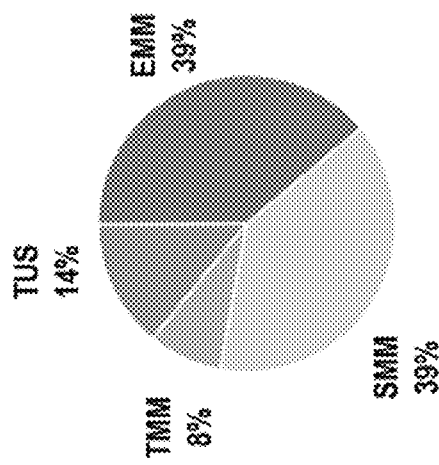
FIGS. 18a-18c demonstrate a histological characterization and localization of tiles of interest in EMM patients with a poor prognosis.
Figure 18A:
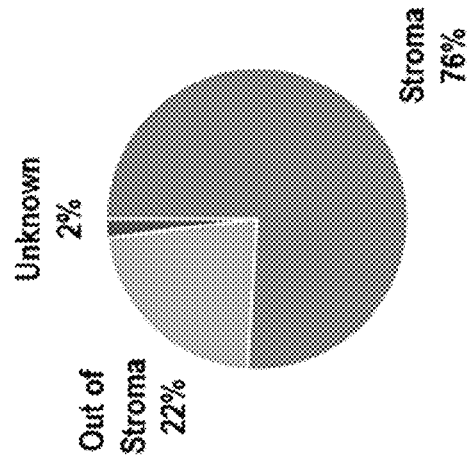

The presence of sarcomatoid patterns in mesothelioma was associated with a worse prognosis across all three subtypes. Here, the tiles associated with low survival in the set of EMM patients with poor prognosis were analyzed. First, it was confirmed that a large proportion of tiles associated with a poor prognosis were associated with a sarcomatoid component (FIG. 16a, 39% of cases), showing that MesoNet helped in detecting sarcomatoid regions that may be missed by pathologists. Second, epithelioid components comprise a large proportion of tiles associated with a poor prognosis (FIG. 18a, 39% of cases), as well as transitional and "unknown" components (FIG. 18a, 22% of cases).

A second analysis showed that the tiles associated with poor survival were mainly located in the stromal regions (FIG. 18b), in concordance with the results described above, validating the importance of the tumor microenvironment.

Figure 18C:
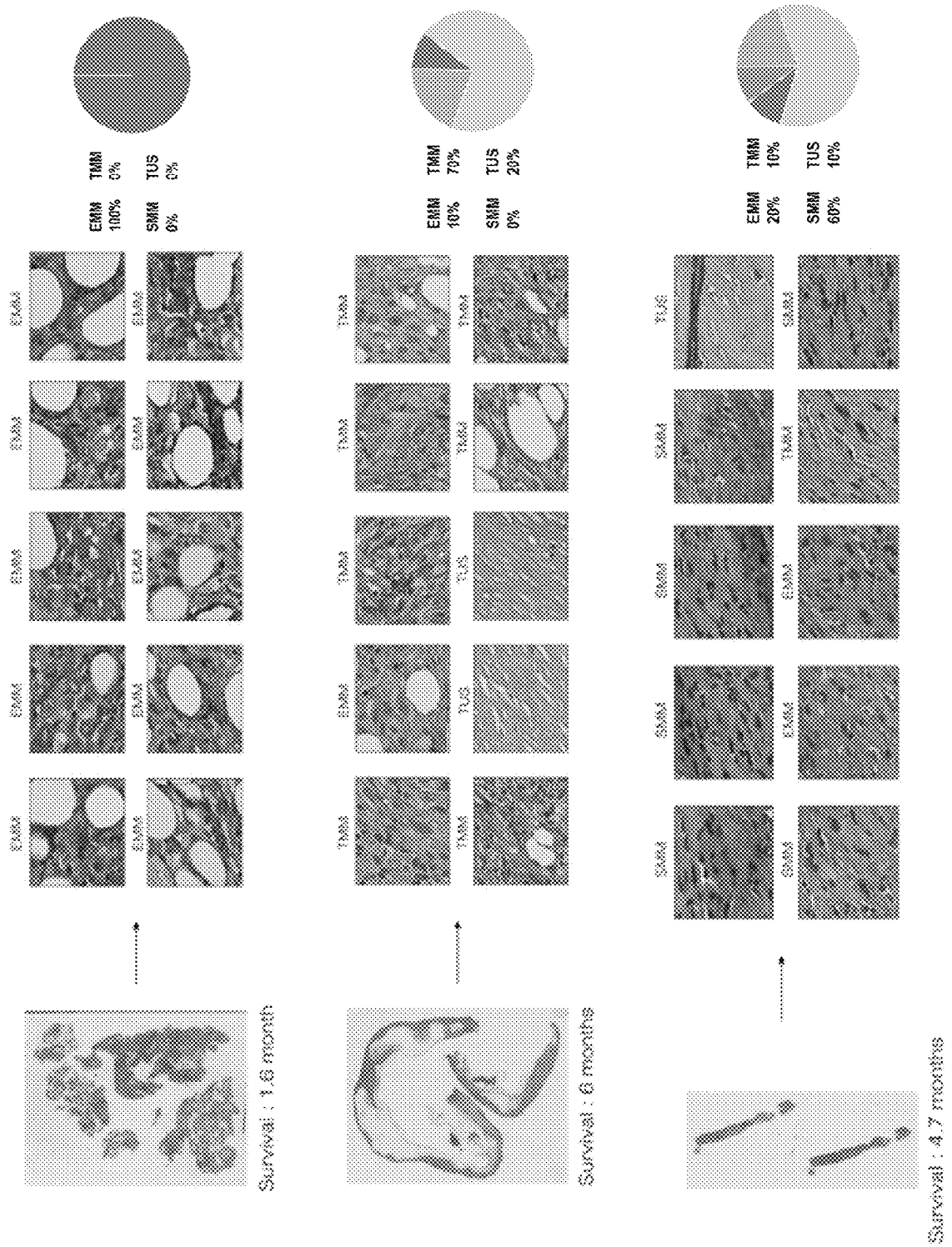

Finally, the tiles associated with a poor prognosis for three EMM patients were visualized. Patient 1 had an overall survival of 1.6 months, but had tiles consisting of epithelioid components only (FIG. 18c). Patient 2 had an overall survival of 6 months and had tiles consisting of mainly transitional components. Finally, Patient 3 had an overall survival of 4.7 months and had mainly sarcomatoid tiles, which might have been missed by the pathologists. Overall, these data show the heterogeneity of the composition of EMM patients with a poor prognosis.

CONCLUSIONS

In conclusion, a deep learning framework for prognosis and prediction in MM based on annotated histology slides is described herein. MesoNet effectively predicts the overall survival of mesothelioma patients solely from whole slide images, in this case whole slide images obtained from large thoracoscopy biopsies or small size needle biopsies. Significantly, MesoNet provides an interpretable framework that gives a score for tiles associated with a good or bad prognosis. This allows the automatic detection of known predictive histological features, such as sarcomatoid components in samples originally classified as epithelioid, which may be useful to aid pathologists to classify patients in the correct subtypes. It also helped identify new predictive histological features independently of the currently recognized cellular subtypes, involving regions not previously known to contribute to prognosis and disease biology, such as stromal regions. This provides a rationale to focus discovery of new targets in these areas.

Figure 19:
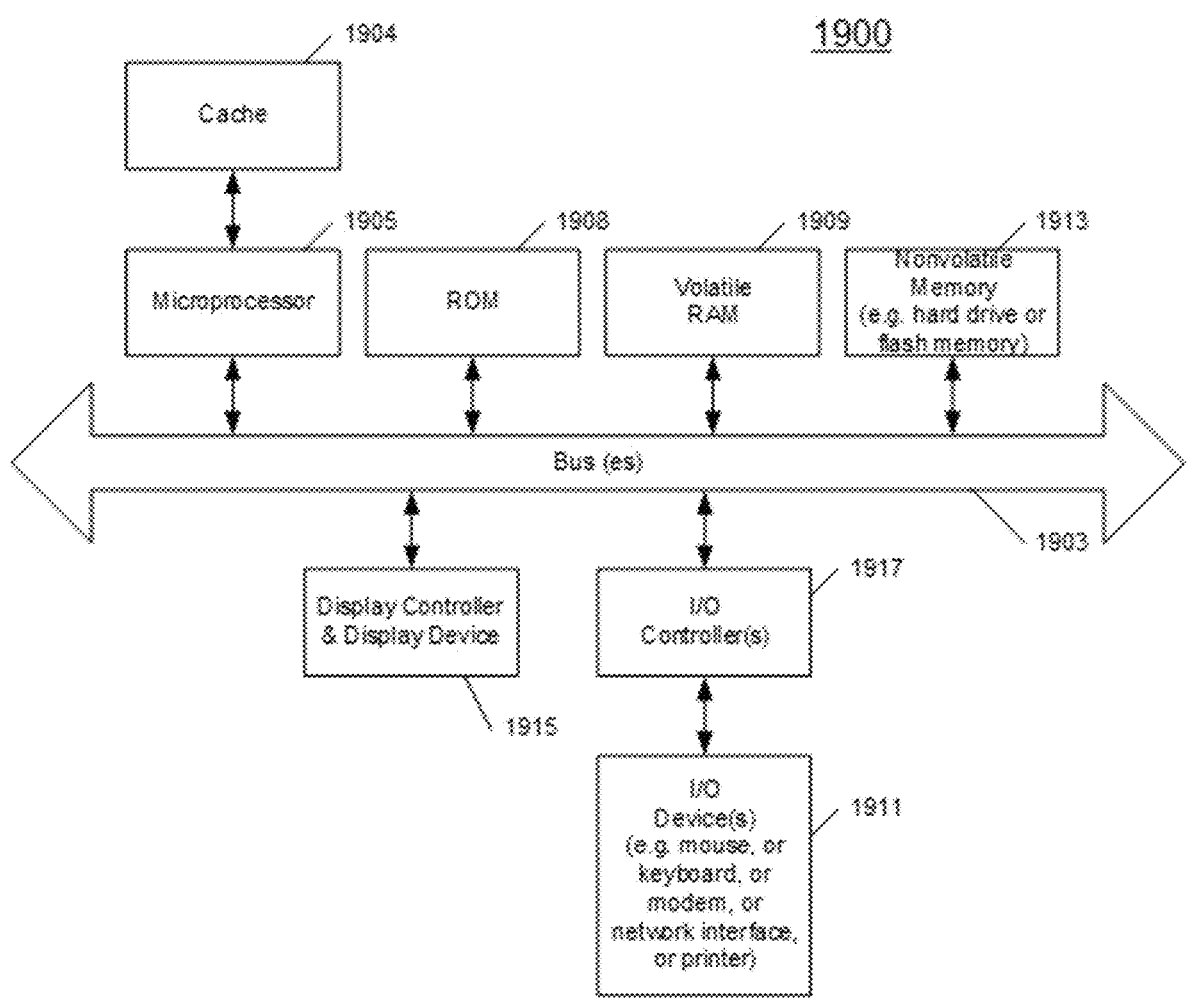
FIG. 19 illustrates one example of a typical computer system, which may be used in conjunction with the embodiments described herein.

FIG. 19 shows one example of a data processing system 1900, which may be used with one embodiment of the present invention. For example, the system 1900 may be implemented including a preprocessing device 102 and/or classifying device 108 as shown in FIG. 1 above. Note that while FIG. 19 illustrates various components of a computer system, it is not intended to represent any particular architecture or manner of interconnecting the components as such details are not germane to the present invention. It will also be appreciated that network computers and other data processing systems or other consumer electronic devices, which have fewer components or perhaps more components, may also be used with the present invention.

As shown in FIG. 19, the computer system 1900, which is a form of a data processing system, includes a bus 1903 which is coupled to a microprocessor(s) 1905 and a ROM (Read Only Memory) 1907 and volatile RAM 19019 and a non-volatile memory 1911. The microprocessor 1905 may include one or more CPU(s), GPU(s), a specialized processor, and/or a combination thereof. The microprocessor 1905 may retrieve the instructions from the memories 1907, 19019, 1911 and execute the instructions to perform operations described above. The bus 1903 interconnects these various components together and also interconnects these components 1905, 1907, 19019, and 1911 to a display controller and display device 19119 and to peripheral devices such as input/output (110) devices which may be mice, keyboards, modems, network interfaces, printers and other devices which are well known in the art. Typically, the input/output devices 1915 are coupled to the system through input/output controllers 1913. The volatile RAM (Random Access Memory) 19019 is typically implemented as dynamic RAM (DRAM), which requires power continually in order to refresh or maintain the data in the memory.

The mass storage 1911 is typically a magnetic hard drive or a magnetic optical drive or an optical drive or a DVD RAM or a flash memory or other types of memory systems, which maintain data (e.g. large amounts of data) even after power is removed from the system. Typically, the mass storage 1911 will also be a random access memory although this is not required. While FIG. 19 shows that the mass storage 1911 is a local device coupled directly to the rest of the components in the data processing system, it will be appreciated that the present invention may utilize a non-volatile memory which is remote from the system, such as a network storage device which is coupled to the data processing system through a network interface such as a modem, an Ethernet interface or a wireless network. The bus 1903 may include one or more buses connected to each other through various bridges, controllers and/or adapters as is well known in the art.

Portions of what was described above may be implemented with logic circuitry such as a dedicated logic circuit or with a microcontroller or other form of processing core that executes program code instructions. Thus processes taught by the discussion above may be performed with program code such as machine-executable instructions that cause a machine that executes these instructions to perform certain functions. In this context, a "machine" may be a machine that converts intermediate form (or "abstract") instructions into processor specific instructions (e.g., an abstract execution environment such as a "virtual machine" (e.g., a Java Virtual Machine), an interpreter, a Common Language Runtime, a high-level language virtual machine, etc.), and/or, electronic circuitry disposed on a semiconductor chip (e.g., "logic circuitry" implemented with transistors) designed to execute instructions such as a general-purpose processor and/or a special-purpose processor. Processes taught by the discussion above may also be performed by (in the alternative to a machine or in combination with a machine) electronic circuitry designed to perform the processes (or a portion thereof) without the execution of program code.

The present invention also relates to an apparatus for performing the operations described herein. This apparatus may be specially constructed for the required purpose, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), RAMs, EPROMs, EEPROMs, magnetic or optical cards, or any type of media suitable for storing electronic instructions, and each coupled to a computer system bus.

A machine readable medium includes any mechanism for storing or transmitting information in a form readable by a machine (e.g., a computer). For example, a machine readable medium includes read only memory ("ROM"); random access memory ("RAM"); magnetic disk storage media; optical storage media; flash memory devices; etc.

An article of manufacture may be used to store program code. An article of manufacture that stores program code may be embodied as, but is not limited to, one or more memories (e.g., one or more flash memories, random access memories (static, dynamic or other)), optical disks, CD-ROMs, DVD ROMs, EPROMs, EEPROMs, magnetic or optical cards or other type of machine-readable media suitable for storing electronic instructions. Program code may also be downloaded from a remote computer (e.g., a server) to a requesting computer (e.g., a client) by way of data signals embodied in a propagation medium (e.g., via a communication link (e.g., a network connection)).

The foregoing discussion merely describes some exemplary embodiments of the present invention. One skilled in the art will readily recognize from such discussion, the accompanying drawings and the claims that various modifications can be made without departing from the spirit and scope of the invention.

The invention claimed is:

1. A method for determining the prognosis of a subject known or suspected to have mesothelioma, comprising:
   accessing a biopsy image obtained from the subject;
   extracting a plurality of feature vectors of the biopsy image by applying a first convolutional neural network, wherein each of the features of the plurality of feature vectors represents local descriptors of the biopsy image and presence or absence of one or more mesothelioma features associated with survival duration;
   classifying the biopsy image using at least the plurality of feature vectors and a classification model, wherein the classification model is trained using a training set of known mesothelioma images and each of the known mesothelioma images has a corresponding label with survival duration information; and
   determining the prognosis of the subject based on at least the classification of the biopsy image, wherein the prognosis is an indication of a survival duration of the subject.

2. The method of claim 1, further comprising:
segmenting the biopsy image into a region of interest that includes information useful for classification and a background region by applying a second convolutional neural network.

3. The method of claim 2, wherein the second convolutional neural network is a semantic segmentation deep learning network.

4. The method of claim 1, further comprising:
tiling a region of interest of the biopsy image into a set of tiles, wherein each of the plurality of feature vectors corresponds to a tile from the set of tiles.

5. The method of claim 4, wherein the tiling comprises:
applying a fixed tiling grid to at least the region of interest, wherein each of the set of tiles has a predetermined size.

6. The method of claim 4, wherein the tiling comprises:
computing a score for each tile in the set of tiles using at least a convolutional 1D layer and the corresponding feature vector for that tile.

7. The method of claim 6, wherein the classification comprises:
applying the classification model to a subset of tile scores to classify the biopsy image.

8. The method of claim 7, wherein the classification model is a multi-layer perceptron with two connected layers.

9. The method of claim 6, wherein the tiling further comprises:
determining the subset of tile scores by,
picking a highest set of tile scores, and
picking a lowest set of tile scores.

10. The method of claim 1, wherein the first convolutional neural network is a ResNet50 neural network.

11. The method of claim 1, wherein the extraction further comprises:
applying an autoencoder on the extracted plurality of feature vectors to reduce a dimensionality of the features of the plurality of feature vectors.

12. The method of claim 1, wherein the training set of known mesothelioma images lacks local annotations of histopathological features.

13. The method of claim 1, wherein the biopsy image lacks local annotations of histopathological features.

14. The method of claim 1, wherein the known mesothelioma prognosis indications represent the duration of survival associated with the known mesothelioma images.

15. The method of claim 1, wherein the prognosis of the subject is a risk score.

16. The method of claim 15, wherein the risk score represents an estimated survival duration.

17. The method of claim 1, wherein the biopsy image is selected from a digitized whole slide image (WSI) and a digitized image of a pathology section obtained from a biopsy stained with hematoxylin and eosin (H&E).

18. A method for generating a classification model for mesothelioma prognosis prediction, the method comprising:
receiving a training set of biopsy images, wherein each of the training set of biopsy images and each of the biopsy images has a label with survival duration information;
for each of the biopsy images in the training set of biopsy images,
extracting a plurality of feature vectors of the biopsy image by applying a first convolutional network, wherein each of the features of the plurality of feature vectors represents local descriptors of that biopsy image and presence or absence of one or more mesothelioma features associated with survival duration; and
training the classification model using at least the extracted feature vectors and the corresponding labels with survival duration information.

19. The method of claim 18, further comprising:
validating the classification model using at least a validation set of biopsy images.

20. The method of claim 19, wherein the validation comprises:
receiving the validation set of biopsy images, wherein each of the validation set of biopsy images has an associated known classification;
for each of the biopsy images in the validation set of biopsy images,
extracting a plurality of feature vectors of that biopsy image by applying a first convolutional neural network, wherein each of the features of the plurality of feature vectors represents local descriptors of that biopsy image,
generating a validation score set for that biopsy image using at least the plurality feature vectors, and
generating a classification for that biopsy image using at least the validation score set and the classification model; and
comparing the plurality of generated classifications with the associated known classifications.

21. The method of claim 20, wherein the comparison of the plurality of generated classifications is performed using an area under the receiver operating characteristic curve (ROC-AUC) comparison, an area under the precision recall curve (PR-AUC) comparison, or a concordance index (c-index) comparison.

22. The method of claim 18, wherein the classification model includes a multi-layer perceptron with two connected layers.

23. The method of claim 18, wherein a biopsy image of the training set or validation set is one of a digitized whole slide image (WSI) and/or a digitized image of a pathology section obtained from a biopsy stained with hematoxylin and eosin (H&E).

24. The method of claim 18, wherein each of the associated known classifications is a known mesothelioma survival value, a known mesothelioma subtype, and/or a known mesothelioma grade.

25. The method of claim 18, wherein the first convolutional neural network is a ResNet50 neural network.

26. The method of claim 18, wherein the extracting of the plurality of feature vectors comprises:
tiling a region of interest of the biopsy image into a set of tiles, wherein each of the plurality of feature vectors corresponds to a tile from the set of tiles.

27. The method of claim 26, wherein the tiling comprises:
applying a fixed tiling grid to at least the region of interest, wherein each of the set of tiles has a predetermined size.

28. The method of claim 27, wherein the training the classification model comprises:
computing a score for each tile in the set of tiles using at least a convolutional 1D layer and the corresponding feature vector for that tile.

29. The method of claim 18, wherein for each of the biopsy images in the training set of biopsy images, the method further comprises:

segmenting that biopsy image into a region of interest that includes information useful for classification and a background region by applying a second convolutional neural network.

30. The method of claim 29, wherein the second convolutional neural network is a semantic segmentation deep learning network.

\* \* \* \* \*